US009205049B2

United States Patent
Reddy et al.

(10) Patent No.: US 9,205,049 B2
(45) Date of Patent: Dec. 8, 2015

(54) TRANSMUCOSAL DELIVERY SYSTEM

(75) Inventors: Deshika Reddy, Stanger (ZA); Oluwatoyin Ayotomilola Adeleke, Roodepoort (ZA); Viness Pillay, Benmore (ZA); Yahya Choonara, Lenasia (ZA)

(73) Assignee: University of the Witwatersrand, Johannesburg, Braamfontein, Johannesburg (ZA)

( * ) Notice: Subject to any disclaimer, the term of this patent is extended or adjusted under 35 U.S.C. 154(b) by 508 days.

(21) Appl. No.: 12/999,911

(22) PCT Filed: Jun. 3, 2009

(86) PCT No.: PCT/IB2009/005831
§ 371 (c)(1),
(2), (4) Date: Jun. 13, 2011

(87) PCT Pub. No.: WO2009/153634
PCT Pub. Date: Dec. 23, 2009

(65) Prior Publication Data
US 2012/0003316 A1  Jan. 5, 2012

(30) Foreign Application Priority Data

Jun. 19, 2008 (ZA) .................... 2007/10999
Nov. 14, 2008 (ZA) .................... 2008/09707

(51) Int. Cl.
*A61K 9/14* (2006.01)
*A61K 9/00* (2006.01)
(Continued)

(52) U.S. Cl.
CPC . *A61K 9/006* (2013.01); *A61K 9/19* (2013.01); *A61K 31/135* (2013.01)

(58) Field of Classification Search
CPC ... A61K 9/2086; A61K 9/205; A61K 9/2054; A61K 9/006
See application file for complete search history.

(56) References Cited

U.S. PATENT DOCUMENTS

| 4,713,243 | A  | * | 12/1987 | Schiraldi et al. ............. 424/676 |
| 2002/0132008 | A1 | * | 9/2002 | Mumper et al. ............. 424/487 |

(Continued)

FOREIGN PATENT DOCUMENTS

| JP | S62 135417 | 6/1987 |
| JP | S62 175413 | 8/1987 |

(Continued)

OTHER PUBLICATIONS

Inouye K, Machida Y, Sannan T, Nagai T. Buoyant sustained release granules based on chitosan. Drug Des Deliv. Jan. 1989;4(1):55-67. (Abstract Only).*

(Continued)

*Primary Examiner* — Lakshmi Channavajjala
(74) *Attorney, Agent, or Firm* — Hamilton, Brook, Smith & Reynolds, P.C.

(57) ABSTRACT

This invention relates to a multi-configured, transmucosal pharmaceutical dosage form and, more particularly, to a pharmaceutical dosage form which has a single monolithic/heterogeneous layer or a plurality of such layers. The dosage form is suitable for the delivery of one or more pharmaceutical compositions via the buccal, sublingual, rectal, vaginal or transmucosal delivery route in a human or animal body. It provides for selected delivery profiles resulting from, but not limited to, a porosity-enabled composite matrix of one or more layers/components of the pharmaceutical composition/s. The invention also provides for a method of manufacturing said transmucosal pharmaceutical dosage form in a plurality of configurations.

3 Claims, 14 Drawing Sheets

An example of a method employed for preparation of a multi-configured dosage form according to the invention.

(51) Int. Cl.
*A61K 9/19* (2006.01)
*A61K 31/135* (2006.01)

(56) References Cited

U.S. PATENT DOCUMENTS

| 2002/0164373 A1* | 11/2002 | Maloney | 424/469 |
| 2008/0014268 A1* | 1/2008 | Cherukuri | 424/472 |
| 2008/0085298 A1* | 4/2008 | Pohl et al. | 424/435 |

FOREIGN PATENT DOCUMENTS

| JP | S63 019152 | 1/1988 |
| JP | 2003 508565 | 3/2003 |
| JP | 2005263704 | 9/2005 |
| JP | 2006 524674 | 11/2006 |
| JP | 2008291010 | 12/2008 |
| JP | 2009 508841 | 3/2009 |
| WO | WO 2004/032843 A2 | 4/2004 |
| WO | WO 2007/034287 A2 | 3/2007 |
| WO | WO 2007/036946 A1 | 4/2007 |

OTHER PUBLICATIONS

International Search Report and Written Opinion, PCT/IB2009/005831, mailing date Oct. 8, 2009.
International Preliminary Report on Patentability, PCT/IB2009/005831, dated Dec. 21, 2010.

\* cited by examiner

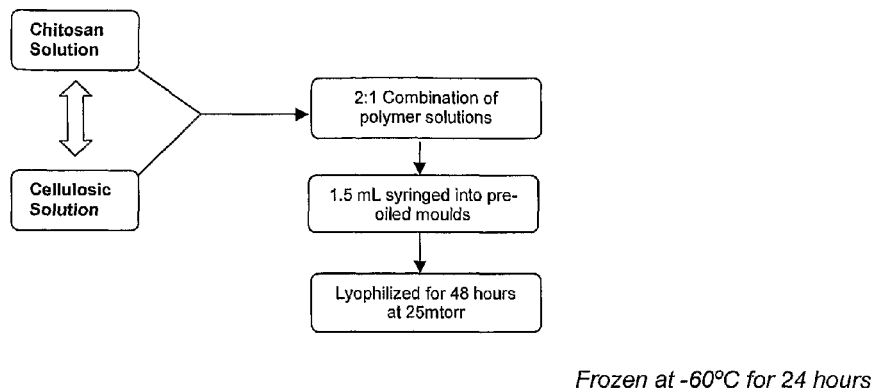
*Frozen at -60°C for 24 hours*
Figure 1　　An example of a method employed for preparation of a multi-configured dosage form according to the invention.
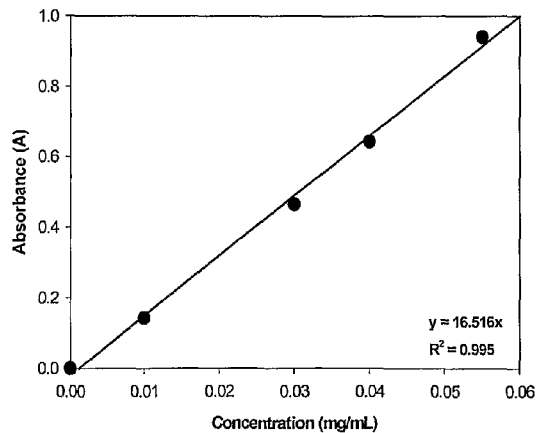
Figure 2　　A calibration curve for phenytoin sodium in simulated saliva pH 6.8 at 206nm (N=4 and standard deviation less than 0.05 in all cases).

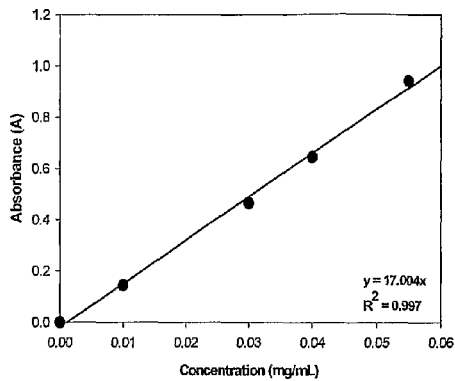
Figure 3    A calibration curve for phenytoin sodium in simulated plasma pH 7.4 at 206nm (N=3 and standard deviation less than 0.047 in all cases).
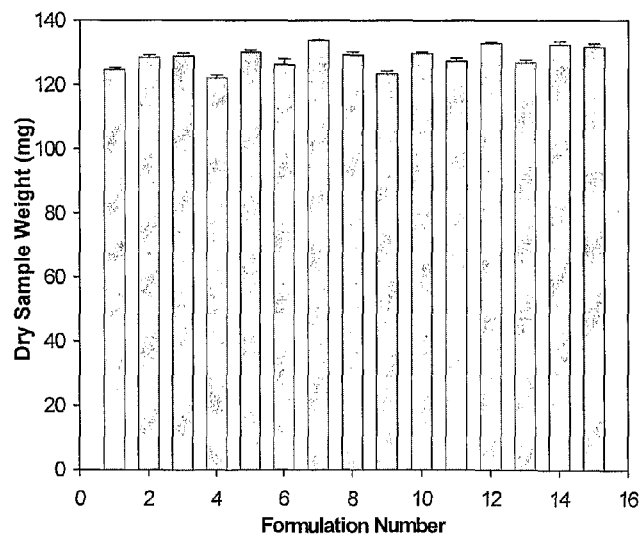
Figure 4    Bar charts showing inter-formulation and intra-formulation weight variations and similarities respectively (N=3, SD ≤ 1.80).

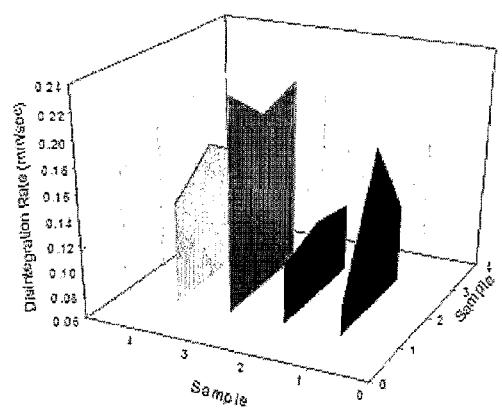
Figure 5   Graphs showing the disintegration rate of pharmaceutical dosage form according to the invention.

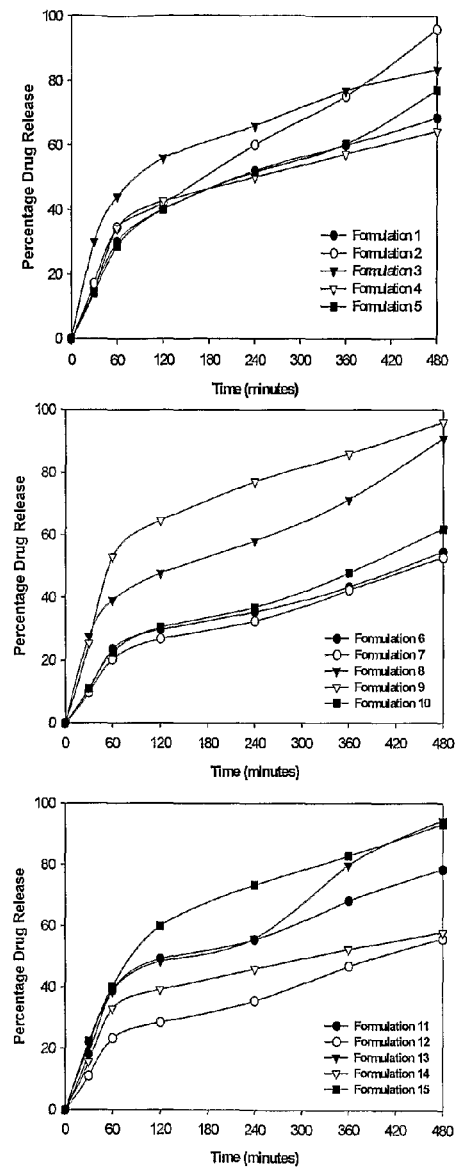
Figure 6   Drug release profiles for 15 formulations in simulated saliva (pH 6.8) prior to optimization (N=3 and SD≤4.56% in all cases).

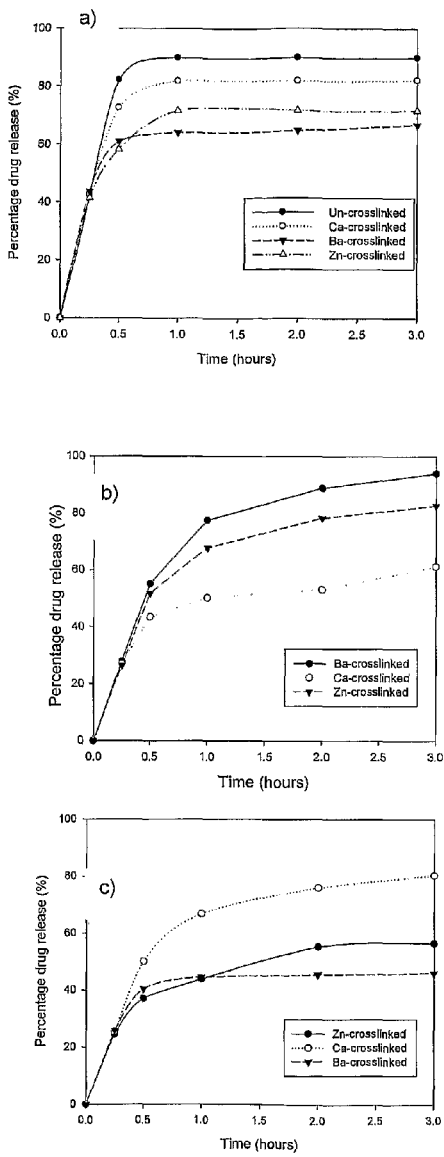
Figure 7  Comparative drug release profiles representing release behaviour from, a) rapid drug release from non-crosslinked formulations and pre-lyophilized crosslinked formulations b) gradual drug release from post-lyophilized crosslinked formulations and c) slow release from pre- and post-lyophilized crosslinked formulations.

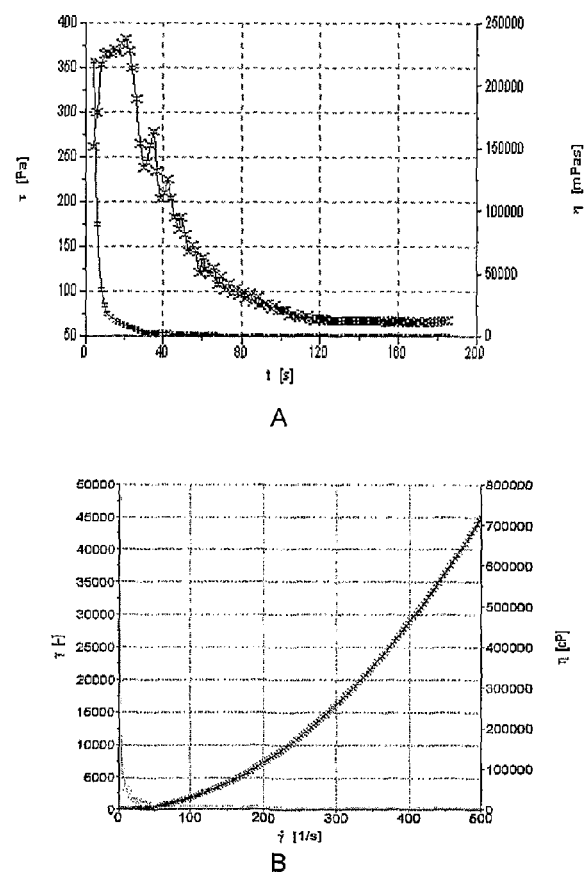
Figures 8A and 8B    Rheological profiles and a typical profile obtained demonstrating the relationship between shear stress, time, and viscosity.

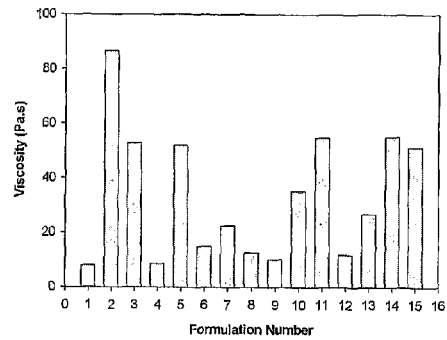
Figure 9   Bar graphs showing ranges of mean viscosity values generated by the homogenous blends of the 15 formulations at a constant shear rate (N=3 and SD≤0.002×10$^{-4}$Pa.s in all cases);
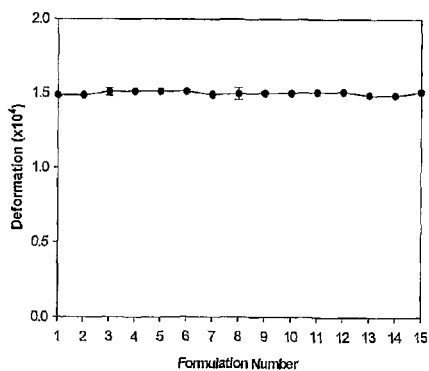
Figure 10   Deformation magnitudes of the homogenous blends of the 15 formulations at a constant shear rate (N=3 in all cases).

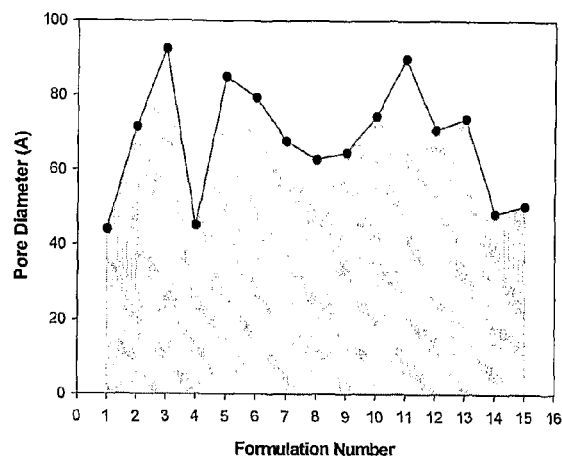
Figure 11   Pore diameters of the 15 formulations showing their mesoporous nature (N=3 in all cases).
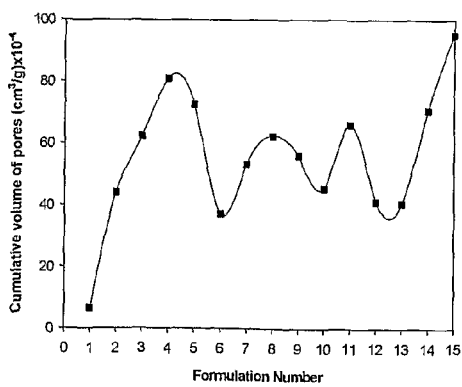
Figure 12   Cumulative volume of pores for the 15 formulations (N=3 in all cases).

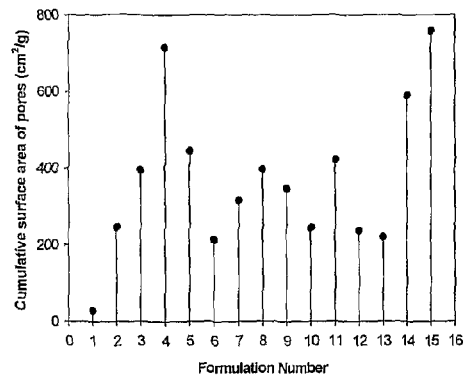
Figure 13    Cumulative surface area of pores for the 15 formulations (N=3 in all cases).
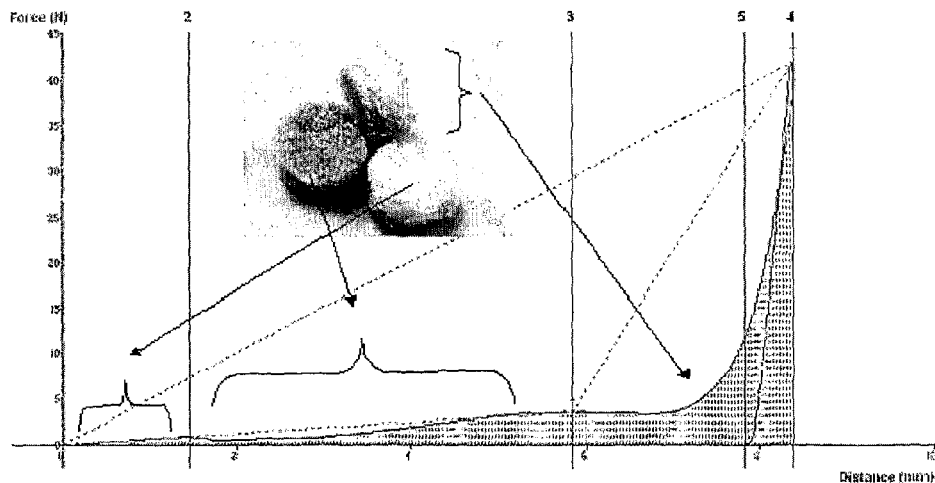
Figure 14    A force-distance profile of a single multi-configured dosage form highlighting distinct textural differences between the cellulosic and chitosan layers respectively as a probe passes completely through the formulation.

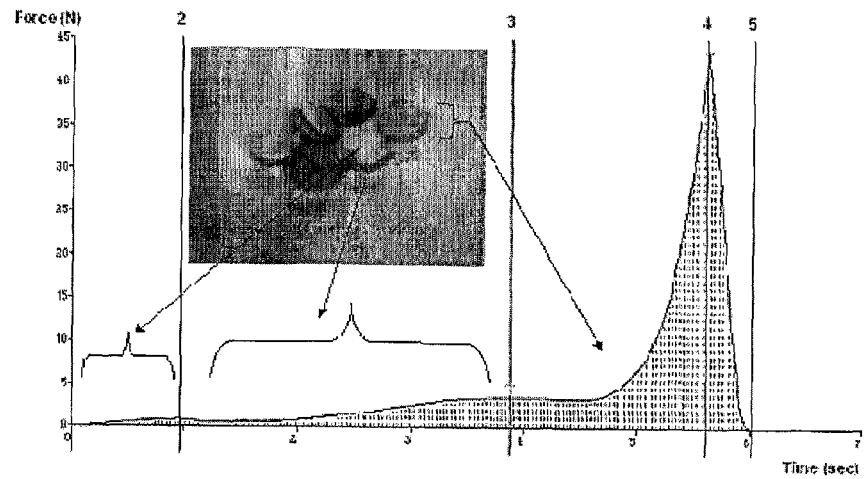

Figure 15  A force-time profile of a single multi-configured dosage form highlighting distinct textural differences between the cellulosic and chitosan layers respectively as the probe passes completely through the formulation.

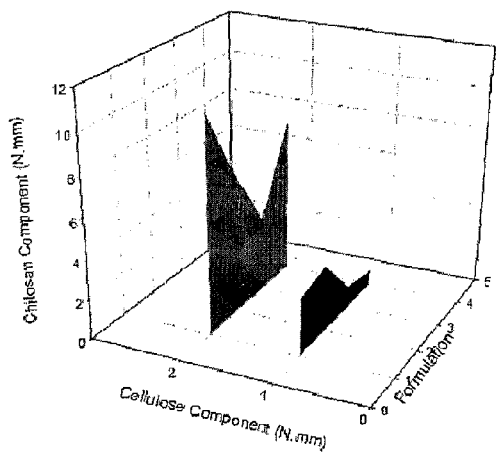

Figure 16  is a graphical representation of the greater degree of matrix tolerance exhibited by the chitosan layer as compared to the cellulosic layer;

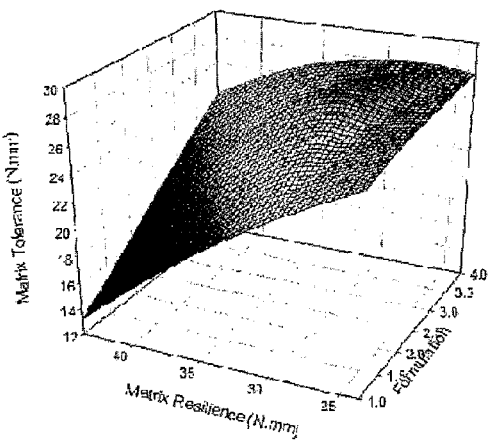
Figure 17   A graphical representation of the overall robustness of the multi-configured pharmaceutical dosage form produced.
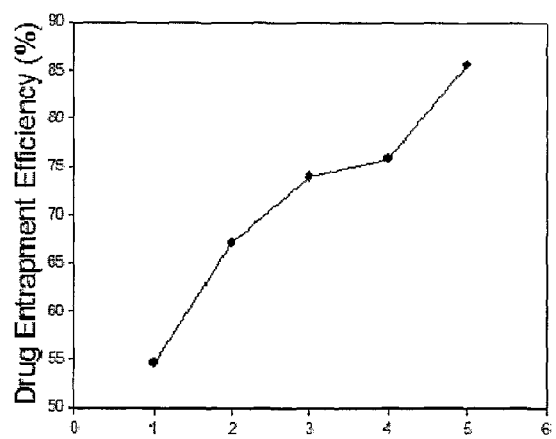
Figure 18   A profile showing the drug entrapment efficiency from the various multi-configured pharmaceutical dosage forms produced.

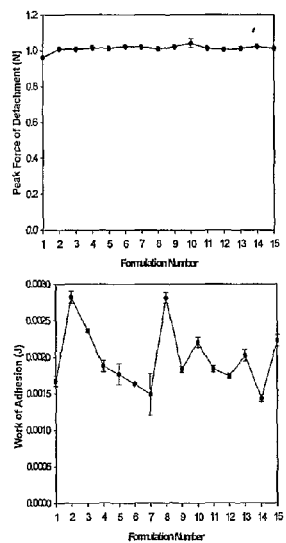
Figure 19  a) peak detachment force in Newton and b) work or energy of bioadhesion of the 15 formulations.
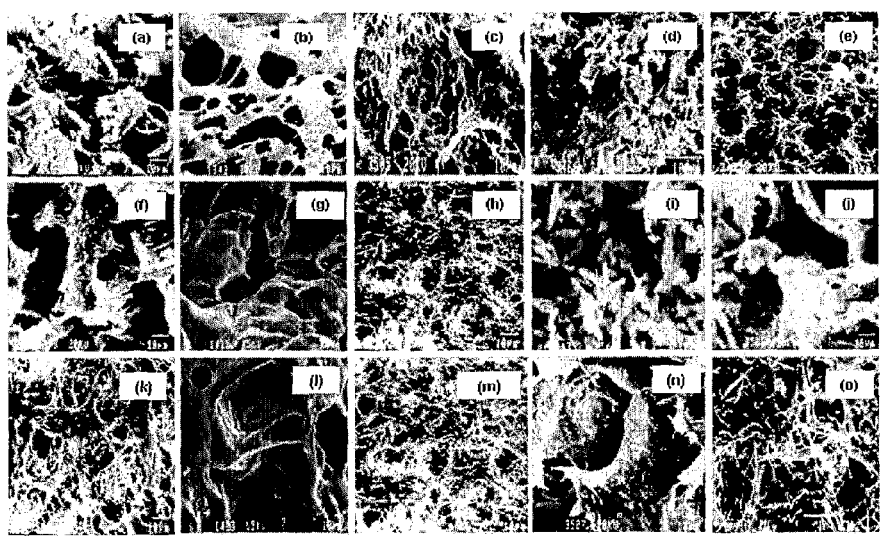
Figure 20  Scanning electron micrographs of the formulations showing the diversity of the pore structures, distributions and interconnections.

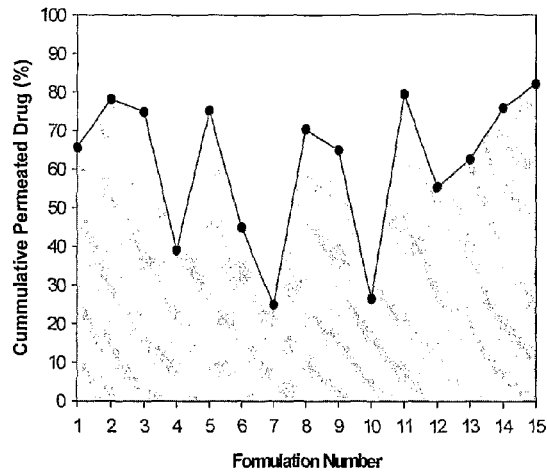
Figure 21  An area plot presenting the cumulative quantity of phenytoin sodium that diffused through the porcine buccal mucosa into the receptor compartment in 8 hours (N=3 and SD≤1.414% in all cases).
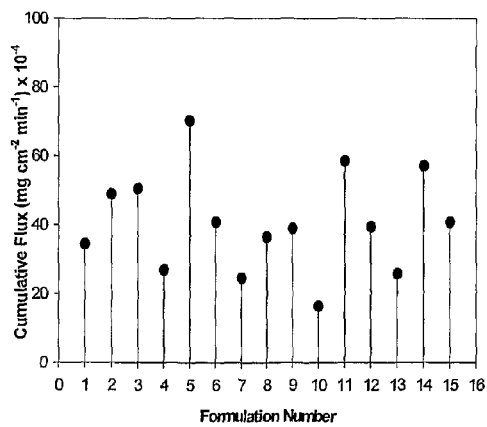
Figure 22  Cumulative steady state flux values computed at 480 minutes for the 15 formulations (N=3 and SD≤1.992×10$^{-4}$mg cm$^{-2}$ min$^{-1}$ in all cases).

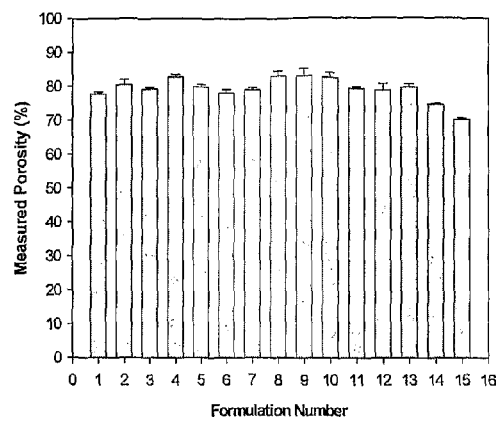
Figure 23    Qualitative measurement of porosity for the pore regulated matrices (N=3 and in all cases).
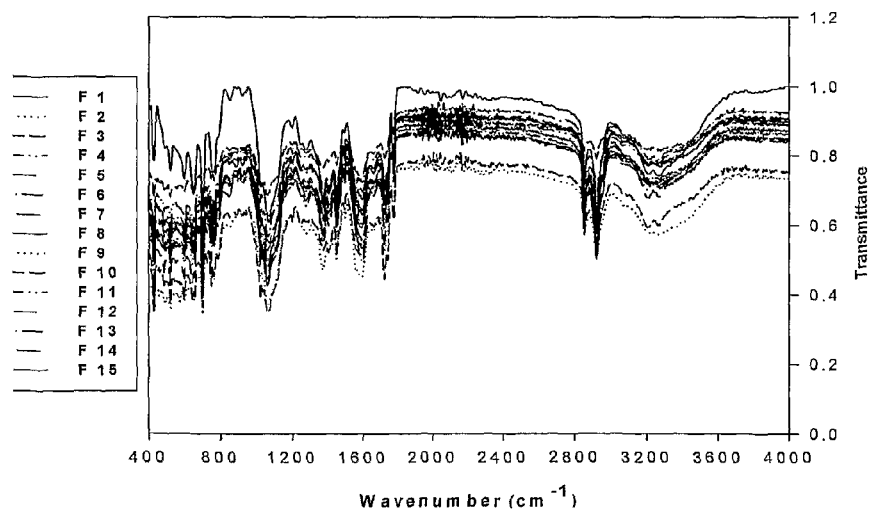
Figure 24    Superimposed FTIR spectra for the 15 formulations.

TRANSMUCOSAL DELIVERY SYSTEM

This application is the U.S. National Stage of International Application No. PCT/IB2009/005831, filed Jun. 3, 2009, which designates the U.S., published in English, and claims priority under 35 U.S.C. §§119 or 365(c) to South Africa Application NO. 2007/10999, filed Jun. 19, 2008, and South Africa Application No. 2008/09707, filed Nov. 14, 2008.

FIELD OF THE INVENTION

This invention relates to a multi-configured pharmaceutical dosage form and, more particularly, to a pharmaceutical dosage form suitable for the delivery of more than one pharmaceutical composition via the buccal, sublingual, rectal, vaginal or transmucosal delivery route in a rate-modulated manner in a human or animal body.

BACKGROUND TO THE INVENTION

Oral drug delivery remains the most popular choice for drug delivery[1], for the ease, convenience, and relative lack of pain during administration results in a high level of patient compliance. As a result, the majority of pharmaceutical dosage forms today are administered in the form of tablets, capsules, powders, granules, or liquids.

Despite their popularity, conventional oral dosage forms are not necessarily the most efficacious. Some patients, particularly geriatrics and pediatrics, have difficulty ingesting solid oral dosage forms[2,3]. This may be as a result of a variety of factors, ranging from the patient suffering from a condition that renders swallowing painful or difficult, to anginophobia (fear of choking)[4,5] or due to the sometimes unpleasant taste. To combat this problem, a variety of rapid-dissolving drug delivery systems have been developed which dissolve in a patient's mouth within a few seconds to minutes of administration thus negating the need to chew or swallow[6]. These systems rely on high levels of disintegrants and/or effervescent agents to achieve their rapid-dissolving properties[7]. However, since most of these dosage forms are still formulated in tablet form, the abovementioned difficulty is still problematic.

Another obvious limitation to oral drug delivery exists in the form of the hostile environment presented by the gastrointestinal tract (GIT) where significant quantities of the administered drug are lost due to acid hydrolysis and the hepatic 'first pass' effect[8-13]. In addition, not all drugs can be incorporated into oral dosage forms due to their specific physicochemical properties. Most importantly, solid oral dosage forms are impractical for the treatment of acute conditions, such as anaphylaxis, where a rapid pharmacological action is required. Drug release from solid oral dosage forms is not immediate since it has to first undergo disintegration and/or dissolution in the GIT prior to releasing the drug[14].

In light of this, alternative routes of drug delivery are being sought. Much attention has been given to transmucosal drug delivery, specifically the buccal cavity, which boasts advantages over parenteral dosage forms without the associated caveats. This can be attributed to the direct drainage of blood from the buccal cavity into the internal jugular vein, thus bypassing the 'first pass' effect[10, 13, 15, 16], and subsequently increasing the bioavailability of poorly bioavailable drugs. The relatively low level of enzymatic activity and a relatively stable pH in the buccal cavity also serves to provide a means for administrating sensitive drugs[10,17]. In addition, these drug delivery systems have a relatively high degree of patient compliance[10].

In general, when the dosage form is placed in the mouth, contact with saliva causes it to disintegrate almost immediately into tiny particles, resulting in liberation of the drug. While still in the oral cavity, some of the drug is absorbed through the oramucosa. Further contact with saliva results in the particles dissolving into a drug loaded suspension. Subsequent swallowing of the remnants of the disintegrated dosage form results in more drug being pre-gastrically absorbed before its passage down the esophagus and into the stomach, where conventional drug absorption processes occur for oral dosage forms. This pre-gastric absorption results in increased bioavailability of the drug since the potentially destructive gastric environment and hepatic metabolism is bypassed. But perhaps the greatest benefit of the rapid disintegrating dosage form is that it combines the advantages of both liquid and conventional solid oral dosage forms. It provides the convenience of a tablet or capsule while simultaneously allowing for the ease of swallowing provided by a liquid formulation[5,18-20].

Whilst much research is being conducted into developing transmucosal drug delivery systems with adequate mucosal tissue permeation, the real challenge lies in developing a system with the abovementioned benefits that is also capable of achieving rapid drug release.

Research interest has, to a great extent, focussed on porous materials or devices which can be described as those possessing characteristic pore and interconnecting structures which influence their function and performance. These materials possess unique properties which can find potential applications as biological tissue scaffolds, in controlled drug delivery, biomaterials engineering, life science and other scientific spheres[21]. These features include their (i) stable and porous configuration, (ii) high surface areas (iii) flexible pore sizes arranged in various distribution patterns and (iv) defined surface properties. These properties provide them with the potential to adsorb/load drug molecules and release them in a reproducible and predictable manner[22].

As indicated above, conventionally, drugs are delivered to the body employing the predominant routes of administration such as oral delivery or injection. The intravenous route which provides rapid physiological relief of symptoms is associated with a high level of pain during administration and may lead to high drug concentrations being injected into the systemic circulation which can be fatal. The oral route of drug delivery offers several advantages in that it is more natural, less invasive and can be painlessly self-administered[23]. However, research has shown that after oral administration, numerous drugs are subject to extensive pre-systemic elimination by gastrointestinal degradation (due to the acidic conditions of the stomach or the presence of enzymes) and/or hepatic metabolism (i.e. the first-pass effect), and the resistance exerted by the intestine may result in low systemic bioavailability, shorter duration of therapeutic activity, and/or formation of inactive or toxic metabolites[24-27].

To circumvent some of the above-mentioned limitations associated with the intravenous and oral routes, transmucosal drug delivery (i.e. delivery of drugs via absorptive mucosa in various easily accessible body cavities such as dermal, buccal, nasal or vaginal) has been explored as an alternative route of administering drugs[28-30]. The transmucosal route of administration also offers the potential for systemic absorption of drugs with plasma profiles closely mimicking that of an injection that makes them useful especially in emergency situations. In addition, mucosal membranes may also be useful sites with good accessibility for easy application of drug delivery systems, especially for those with bioadhesive qualities. With the development of transmucosal drug delivery systems having controlled drug release characteristics, the mucosa can be explored for the non-invasive systemic, sustained delivery of drugs[31].

Thus far, the investigations on transmucosal drug delivery focused extensively on the use of formulations that are not actively porosity-enabled such as tablets, gels, hydrogels, micro-matrices, films, and pastes[32-37]. As far as we know, limited explorative studies exist on the development and mechanistic evaluation of porosity-enabled matrices employed for prolonged systemic drug delivery through mucosal sites. Porosity-regulated formulations can be described as superior to conventional formulations for transmucosal administrations in terms of their morphological flexibility (due to the presence of elastic pores) which can allow for easy manipulation of their drug loading efficiency and rate of drug delivery as well as enhance bioadhesion to mucosal sites and permeation enhancement for systemic delivery of drug molecules[38,39]. In recent years, the demand for such sophisticated approaches for the delivery of therapeutic agents has been on the increase[40]. Commonly existing porous drug delivery systems include: implants[41], scaffolds[42,43], hydrogels[44], ceramics[45-48], drug carriers[49], biocomposites[50], sponges[51], microcapsules[52], wafers[53,55], membranes[58,57] and nanoparticles[58] for various biomedical applications.

In this specification the following terms have the following meanings and the specification and claims should be construed accordingly:

"Multi-configured" when used in conjunction with a pharmaceutical dosage form means that the dosage form has at least two release rate controlling upper and lateral surfaces of varying geometries in their lateral and/or axial planes that are adjacent to each other or a third layer, the said layers preferably being discoid in shape.

"Pore-regulated" when used in conjunction with a pharmaceutical dosage form means that the dosage form is able to modulate the rate of release of an active pharmaceutical compound or compounds on the basis of the size, and/or extent and/or distribution of pores introduced, or formed as a result in the matrix or matrices of the pharmaceutical dosage form.

"Monolithic" when used in conjunction with a pharmaceutical dosage form means that the pharmaceutical dosage form comprises a single polymeric matrix layer in which one or more active pharmaceutical compounds are homogeneously dispersed.

"Heterogeneous" when used in conjunction with a pharmaceutical dosage form means that the dosage form comprises a plurality of layers, preferably two, in which an active pharmaceutical compound or compounds are homogenously dispersed in each layer or in a single layer only.

OBJECT OF THE INVENTION

It is an object of this invention to provide a multi-configured, transmucosal pharmaceutical dosage form, more particularly pharmaceutical dosage form comprising a single monolithic/heterogeneous layer or a plurality of layers which is suitable for the delivery of one or more pharmaceutical compositions via the buccal, sublingual, rectal, vaginal or transmucosal delivery route in a human or animal body and which provides for selected delivery profiles, from but not limited to, a porosity-enabled composite matrix of one or more layers/components of the pharmaceutical composition/s and to provide a method of manufacturing said transmucosal pharmaceutical dosage form in a plurality of configurations.

SUMMARY OF THE INVENTION

In accordance with this invention there is provided a multi-configured, transmucosal pharmaceutical dosage form comprising at least one multi-configured, porous, low-density, hydroscopic, mucoadhesive, pore-regulated, composite polymeric matrix having at least one desired pharmaceutically active compound added thereto, the matrix reacting with at least one mucosal surface stimulus to facilitate the release of the desired pharmaceutically active compound in use.

There is also provided for the dosage form to have a single polymeric matric having at least one desired pharmaceutically active compound added thereto, alternatively there is provided for the dosage form to have one or more polymeric matrices, preferably layered about a central core polymeric matrix and for each polymeric matrix to have at least one desired pharmaceutically active compound added thereto.

There is also provided for the polymeric matrix to regulate an influx of body fluids into the polymeric matrix and, consequently, release of the desired pharmaceutically active compound, preferably by a leaching of the compound from the polymeric matric, at its preferred administration site and for the regulation of the influx of body fluids into the polymeric matrix to be achieved by variations in the size, extent and distribution of pores in the polymeric matrix.

There is further provided for the desired pharmaceutically active compound to be blended with the polymer to form a homogenous compound, alternatively for the desired pharmaceutically active compound to be in the form of micro-pellets, alternatively nano-pellets, which are mixed with the polymer. Still further alternatively there is provided for the desired pharmaceutically active compound to be in the form of at least one discrete pellet, preferably a discoid pellet, alternatively an elongate cylinder, and for said pellet or pellets to be embedded in the polymeric matrix alternatively for the pellet or pellets to be incorporated into a layer of a multilayered dosage form and for the polymeric matrix to have a known dissolution and/or erosion rate in response to known stimuli and which determines the rate and location at which the pharmaceutically active compound is released from the dosage form and made available for absorption.

There is further provided for the pharmaceutical dosage form to be orally ingestible and for it to contain a first pharmaceutically active composition for delivery to the buccal cavity of a human or animal and at least a second pharmaceutically active composition in the form of or more pellets which, in use once the polymeric matrix to which the first pharmaceutically active compound is added has dissolved, are swallowed thus delivering the pharmaceutically active compound contained in the pellet or pellets to another region of the human or animal body, preferably the gastrointestinal tract, for absorption.

There is further provided for the polymeric matrix to react, in use, with at least one mucosal surface stimulus by adhering to the mucosal surface, alternatively by forming a gel, further alternatively by forming a diffusive barrier which dissolves over a predetermined time period, and, still further alternatively, by undergoing a polymorphic transformation, to release the pharmaceutically active compound.

There is also provided for the dosage form to include one or more adjuvants such as: permeation enhancers, disintegration agents, flavoring agents, plasticizers, pore formers, matrix stiffeners, stabilizers, surfactants, deliquescent materials, binders, and aqueous or non-aqueous inorganic or organic solvents.

There is also provided for the pharmaceutical dosage form to be multilayered with at least one rapid releasing layer and one prolonged, or sustained release layer and for each layer including at least one desired active pharmaceutical compound which is released and, thus available for absorption immediately or over a prolonged period of time depending on which layer it forms a part of.

There is also provided for the polymeric matrix of the rapid release layer to be a low-density matrix of a monolithic or heterogeneous form, and for the polymeric matrix to have a density of between about $1 \times 10^3$ kg/m$^3$ and about $5 \times 10^3$ kg/m$^3$ when calculated using the mathematical relationship; $\rho = m/V$, where, $\rho$=density, m=mass of the said pharmaceutical dosage form and V=volume occupied by the said pharmaceutical dosage form in an appropriate mould. Preferably the appropriate mould should have a diameter of about 14 mm, a height of about 8 mm and a volume of between about 30 and about 60 mm$^3$.

There is also provided for the polymeric matrix of the sustained release layer to be a high-density matrix of the monolithic or heterogeneous form and for the polymeric matrix to have a density of between $5 \times 10^3$ kg/m$^3$ and $10 \times 10^3$ kg/m$^3$ when calculated using the mathematical relationship; $\rho = mN$, where, $\rho$=density, m=mass of the said pharmaceutical dosage form and V=volume occupied by the said pharmaceutical dosage form in an appropriate mould, preferably having a diameter of about 14 mm, a height of about 8 mm and a volume between about 30 and about 60 mm$^3$.

There is further provided for the polymer to be a hydrophilic swellable polymer, preferably one or more polymers selected from the group consisting of: hydroxypropyl cellulose (HPC), polymethacrylate, polyamide, polyesters, polyvinyl alcohol (PVA), polyacrylic acid (PAA), hydroxypropylmethyl cellulose (HPMC), hydroxyethylcellulose (HEC), polyethylene oxide (PEO), sodium alginate, chitosan and pectin, for the polymers to be mixed with a copolymer which alters the drug release and/or the physicochemical and/or physicomechanical properties of the polymer, for the copolymer to be a wax, a hydrosoluble agent or another polymer such as polyethylene glycol or chitosan, and/or excipient/s from among the group consisting of lipidic esters, glycine, esterified glycerides, mannitol or lactose.

There is also provided for the polymeric matrix to be formed by a single polymer or from a blend of polymers and, in the case of a blend of polymers for the blend to be a physical polymer blend or chemical polymer blend, preferably selected from the group consisting of polyoxylglycerides and/or polyglycolized triglycerides.

There is further provided for the pharmaceutical dosage form to have self-emulsifying properties and for the dosage form to function as a co-emulsifier or penetration enhancer for enhancing transmucosal solubilization and absorption of the active pharmaceutical composition or compositions.

There is further provided for the pharmaceutical dosage form to include substances having low hydroxyl values which, in use, lower reactivity towards sensitive pharmaceutically active compounds.

There is further provided for the pharmaceutical dosage form to include substances incorporating emulsifiers which, in use, improve the dispersibility of the pharmaceutically active compounds, the emulsifiers having a with a desired hydrophile lipophile balance (HLB) value, preferably ranging from 1 to 14.

There is further provided for the polymeric matrix to be a low-density matrix, alternatively a pore-regulated matrix, further alternatively a porous spongy lyophilized matrix, for the dosage form to have at least two polymeric matrix layers, for one layer to dissolve, alternatively disintegrate, rapidly in use and for the other layer to dissolve, alternatively disintegrate, over a prolonged or sustained period in use thus allowing for a time-controlled delivery of pharmaceutically active compounds incorporated into the layers.

There is also provided for the polymer to be HPC which is included in the dosage form at a concentration of 1% w/v and for the dosage form to further include a bulking agent excipient, preferably lactose, at a concentration of 6% w/v, a disintegrant, preferably sodium starch glycolate at a concentration of at least 2% w/v, a taste masker, preferably a β-cyclodextrin or β-cyclodextrin complex, at a concentration at a concentration equivalent to at least 5 times that of the quantity of pharmaceutically active ingredients added to it, and at least one pharmaceutically active composition which is an antiretroviral (ARV), preferably zidovudine, and/or an antihistamines, preferably diphenhydramine hydrochloride.

There is also provided for the polymer or polymer blend forming the polymer matrix to have a selected pharmaceutical HLB value, for the polymer or polymer blend to be a swellable polymer or polymer blend, alternatively a hydrophillic swellable polymer or polymer blend, further alternatively a lipophilic swellable polymer or polymer blend, and for the polymer or polymer blend to be mixed with at least one copolymer which alters its physicochemical properties, alternatively with at least one copolymer which alters its physicochemical properties, still further alternatively with at least one copolymer which alters its physicochemical and physicomechanical properties.

There is also provided for the polymer to include a second polymer, preferable polyethylene glycol.

There is further provided for the transmucosal pharmaceutical dosage form in to include one or more pharmaceutically active compounds which are selected from the group consisting of: analgesics, sedatives, antihistamines, pediatric drugs and antiretroviral drugs and their pharmaceutically active isomers.

There is also provided for the transmucosal pharmaceutical dosage form to be administrable to pediatric or geriatric patients and for the pharmaceutically active compound to be selected from the group consisting of analgesics, preferably an analgesic selected from the group consisting of: diclofenac, aspirin and paracetamol and their pharmaceutically active isomers, sedatives, preferably a sedative selected from the group consisting of: diazepam, zolpildem and zopiclone and their pharmaceutically active isomers, antihistamines, preferably an antihistamine selected from the group consisting of: loratadine, chlorpheniramine or diphenhydramine, antiretroviral drugs, preferably zidovudine, multivitamins, minerals, trace elements, phytonutrients and their pharmaceutically active isomers.

There is also provided for the said transmucosal pharmaceutical dosage form to deliver, in use, fixed-dose combinations of pharmaceutically active compounds which are usually administered as a regimen and, preferably paracetamol and tramadol.

There is also provided for the pediatric drug, multivitamin, phytonutrients, mineral or trace element to be selected from the group consisting of: nystacid, hyoscine, zidovudine, ascorbic acid, vitamin D, calcium, selenium, ginseng and their pharmaceutically active isomers.

There is further provided for the polymeric matrix of the pharmaceutical dosage form to be in the form of a spongy matrix, for the matrix to have a flexible mean viscosity of at least $1 \times 10^4$ Pa·s, and for at least one layer of the matrix to have an average pore diameter of at least 40 Å, cumulative surface area and pore volume of at least 28 cm$^2$/g and $6.5 \times 10^{-4}$ cm$^3$/g respectively and a quantitative and qualitative porosity of at least 70%.

There is further provided for the pharmaceutical dosage form to have a composite porosity-enabled matrix that can be loaded with at least one active pharmaceutical compound and/or thermo-labile compositions for therapeutic or prophylactic applications in a human or animal body.

There is also provided for the pharmaceutical dosage form to achieve a flexible, rate-modulated systemic delivery of zero-order kinetics for constant drug plasma levels from at least one layer of a multi-layered system or a single matrix of the pharmaceutical dosage form to minimize high fluctuations of plasma levels and frequency of administration of active pharmaceutical composition/s in a human or animal body.

There is also provided for the pharmaceutical dosage form to have a composite porosity-enabled matrix in which the physical, physicochemical and physicomechanical properties of the homogenous polymer blend can be modified by polymeric compounds, inorganic and/or organic solvents as well as other formulation additives, to achieve the desired release of active pharmaceutical composition/s from at least one or a single matrix and biodegradation characteristics of the drug delivery system and, consequently, modulate the release of an active pharmaceutical composition.

There is further provided for the pharmaceutical dosage form to administered at least one pharmaceutically active composition through the buccal, sublingual, vaginal, rectal, dermal, intramuscular, subcutaneous, intracutaneous, anal and intranasal routes and for the polymeric matrix to be mouldable into a shape and size suitable for the mode of administration of the pharmaceutical dosage form.

There is also provided for a porosity-enabled pharmaceutical dosage form in which the at least one layer or a single matrix of the said dosage form and active pharmaceutical composition/s are formed into a pharmaceutical dosage form suitable for dermal applications as dry, flowable powders for the delivery of relevant topical active pharmaceutical compositions.

There is also provided for a pharmaceutical dosage form wherein at least one polymeric matrix layer or a single matrix has a surface structure that is porous and can comprise of flexible and varying pore configurations, pore volume of distributions and nature of interconnecting barriers which can influence the release kinetics of active pharmaceutical composition/s and are dependent on the composition of the interphase, co-particulate, co-solvent, homogenization method of production.

There is also provided for the polymeric matrix or matrices to consist of hydrophilic or hydrophobic, biocompatible, biodegradable polymeric materials, preferably selected from the group consisting of: ethylcellulose, polylactic acid, polyacrylic acid, polymethacrylate, polyvinyl alcohol, gelatin, polyamides, polyoxylglycerides and chitosan, for the materials to crosslinked, in use, thus providing a modification in the quantity and time of release of an active pharmaceutical composition from the said pharmaceutical dosage form, and for the materials to be crosslinked with a crosslinking or complexation agent from among the group of metal salts or the Hofmeister series of salts.

There is also provided for the polymeric materials to be prepared from a pre-lyophilized crosslinking step in which crosslinking solutions, preferably from among the group comprising zinc sulphate, barium chloride, or calcium sulphate, in at least a 1:0.75 ratio of crosslinker to polymer, depending on the physiochemical or physicomechanical properties of the polymer employed, are added thereto. Alternatively there is provided for the polymeric materials to be prepared from a post-lyophilized crosslinking step in which various crosslinking solutions, preferably from among the group comprising zinc sulphate, barium chloride, or calcium sulphate in at least 2:1.5 ratio of crosslinker to polymer, or alternatively, depending on the physiochemical or physicomechanical properties of the polymer employed, are added thereto. Further alternatively there is provided for the polymeric materials to be prepared from both a pre-lyophilized and a post-lyophilized crosslinking step in which various crosslinking solutions, preferably from the group consisting of zinc sulphate, barium chloride, and calcium sulphate, are added thereto.

The invention extends to a method of producing a multi-configured, transmucosal pharmaceutical dosage form comprising at least one multi-configured, porous, low-density, hydroscopic, mucoadhesive, pore-regulated, composite polymeric matrix having at least one desired pharmaceutically active compound added thereto, the matrix reacting with at least one mucosal surface stimulus to facilitate the release of the desired pharmaceutically active compound as described above in which an interphase, co-particulate, co-solvent, homogenization technique which encompasses preparing a multi-component co-solvent based homogenous co-particulate blend that is loaded with the active pharmaceutical composition/s and eliminating the co-solvents employed by lyophilization to form porous interconnecting structures is used.

There is also provided for the method to obviate the application of external heat during preparation of the dosage form, for the said blend of the said pharmaceutical dosage form to be a homogenous or heterogeneous lipoid, for lyophilization of the dosage form to involve removing bound moisture from the polymeric matrix or matrices thus enhancing the stability and longevity of the active pharmaceutical compositions.

There is also provided for the method to include altering the lyophilization time during preparation to as to vary the integrity of at least one layer of or of the entire matrix of the dosage form and, thus, influence the rate of outward diffusion of active pharmaceutical composition/s therefrom, in use, when exposed to an aqueous-based acidic, neutral or basic medium or bodily fluids by causing a polymeric relaxation reaction to occur in a predictable time dependent manner from the operatively outer boundaries of the matrix towards the operatively inner boundaries thereof and, consequently, limit outward diffusion of the active pharmaceutical composition/s.

There is also provided for the method to include freezing the polymer suspension for 12 to 24 hours before lyophilizing for between 12 and 48 hours.

DESCRIPTION OF THE PREFERRED EMBODIMENTS

Embodiments of the invention will be illustrated by the following non-limiting examples in an attempt to address the delivery of multiple APIs in a site-specific manner and, more particularly, in a single multi-configured dosage form. Regard will also be had to the accompanying Figures in which:

FIG. 1 is an example of a method employed for preparation of a multi-configured dosage form according to the invention;

FIG. 2 is a calibration curve for phenytoin sodium in simulated saliva pH 6.8 at 206 nm (N=4 and standard deviation less than 0.05 in all cases);

FIG. 3 is a calibration curve for phenytoin sodium in simulated plasma pH 7.4 at 206 nm (N=3 and standard deviation less than 0.047 in all cases);

FIG. 4 shows bar charts showing inter-formulation and intra-formulation weight variations and similarities respectively (N=3, SD≤1.80);

FIG. 5 is a series of graphs showing the disintegration rate of pharmaceutical dosage form according to the invention;

FIG. 6 illustrates drug release profiles for 15 formulations in simulated saliva (pH 6.8) prior to optimization (N=3 and SD≤4.56% in all cases);

FIG. 7 graphically illustrates comparative drug release profiles representing release behaviour from, a) rapid drug release from non-crosslinked formulations and pre-lyophilized crosslinked formulations b) gradual drug release from post-lyophilized crosslinked formulations and c) slow release from pre- and post-lyophilized crosslinked formulations;

FIGS. 8A and 8B show rheological profiles and a typical profile obtained demonstrating the relationship between shear stress, time, and viscosity;

FIG. 9 bar graphs showing ranges of mean viscosity values generated by the homogenous blends of the 15 formulations at a constant shear rate (N=3 and SD≤0.002×10$^{-4}$ Pa·s in all cases);

FIG. 10 a graph showing deformation magnitudes of the homogenous blends of the 15 formulations at a constant shear rate (N=3 in all cases);

FIG. 11 a graph of pore diameters of the 15 formulations showing their mesoporous nature (N=3 in all cases);

FIG. 12 a graph showing the cumulative volume of pores for the 15 formulations (N=3 in all cases);

FIG. 13 a graph of the cumulative surface area of pores for the 15 formulations (N=3 in all cases);

FIG. 14 shows a force-distance profile of a single multi-configured dosage form highlighting distinct textural differences between the cellulosic and chitosan layers respectively as a probe passes completely through the formulation;

FIG. 15 shows a force-time profile of a single multi-configured dosage form highlighting distinct textural differences between the cellulosic and chitosan layers respectively as the probe passes completely through the formulation;

FIG. 16 is a graphical representation of the greater degree of matrix tolerance exhibited by the chitosan layer as compared to the cellulosic layer;

FIG. 17 is a graphical representation of the overall robustness of the multi-configured pharmaceutical dosage form produced;

FIG. 18 is a profile showing the drug entrapment efficiency from the various multi-configured pharmaceutical dosage forms produced;

FIG. 19 shows a) peak detachment force in Newton and b) work or energy of bioadhesion of the 15 formulations;

FIG. 20 is a series of scanning electron micrographs of the formulations showing the diversity of the pore structures, distributions and interconnections;

FIG. 21 is an area plot presenting the cumulative quantity of phenytoin sodium that diffused through the porcine buccal mucosa into the receptor compartment in 8 hours (N=3 and SD≤1.414% in all cases);

FIG. 22 shows cumulative steady state flux values computed at 480 minutes for the 15 formulations (N=3 and SD≤1.992×10$^{-4}$ mg cm$^{-2}$ min$^{-1}$ in all cases);

FIG. 23 provides an indication of the qualitative measurement of porosity for the pore regulated matrices (N=3 and in all cases); and FIG. 24 is a series of superimposed FTIR spectra for the 15 formulations.

In order to explore the processes involved in the fabrication and mechanistically evaluate the porosity-enabled composite multi-configured pharmaceutical dosage form for rapid and/or sustained transmucosal drug delivery, the buccal mucosa was employed as a model transmucosal site. The transbuccal route among the various transmucosal sites is most suitable for administration of rapid and/or retentive dosage forms due to (i) its excellent accessibility for self administration, (ii) short recovery times after stress or damage, (iii) presence of an expanse of robust, smooth muscle, (iv) rich blood supply, (v) direct access to the systemic circulation through the internal jugular vein which allows drugs to bypass the pre-systemic metabolic processes thus leading to an increased bioavailability (Alur, et al., 2001; Sudhakar et al., 2006). Other advantages such as painless administration, versatility and simplicity, easy dosage form withdrawal whenever desired and the ability to include permeation enhancers, enzyme inhibitors, pH modifiers or bioadhesive polymers in the formulation for local or systemic action make systems constructed for transbuccal drug delivery purposes a promising option in effective pharmacotherapy (Zhang et al., 1994; Lee, 1988; Alur, et al., 2001; Attia et al., 2004; Sudhakar et al., 2006). An interphase, co-particulate, co-solvent, homogenization technique coupled with lyophilization were utilized to form the multi-configured pharmaceutical dosage form. The capability of this method of production to generate a variety of porosity-enabled formulations with layering and demonstrating flexible qualities were achieved by varying the concentrations of both the solvent and biocompatible, biodegradable, non-toxic solute components that produced the homogenous and heterogeneous blends which is lyophilized to remove the solvent molecules and produce the single or multi-layered formulation. The choice of method of preparation and modifications were based on simplicity and optimum efficiency in generating robust formulations which enables an undemanding process operation and a minimized production cost enhancing patient affordability. The physicochemical and physicomechanical properties of the formulations to suit the intended applications were elucidated to provide comprehensive information on its formation and functioning as this is a newly configured technology. This study was guided through a statistically robust experimental design approach and the characteristics measured included formulation mass, in vitro drug release behaviour, matrix resilience, energy of matric deformation, matrix firmness, drug loading efficiency, ex vivo bioadhesive capacity, rheological assessments of blends, surface morphology, ex vivo permeation induction and enhancement, qualitative and quantitative evaluation of matrix porosity and elucidation of possible structural transitions.

Materials and Methods

Materials

Chitosan (food grade) and menthol were obtained from Warren Chem Specialties, Johannesburg, South Africa. Gelatine, carbamazepine, phenytoin sodium, polyvinyl alcohol ($M_w$=72,000 g/moL), magnesium stearate, were purchased from Sigma Chemical Company (St. Louis, USA). Sorbitan ester 80 (span 80) and ethanol (95%) were procured from Merck Chemicals (Darmstadt, Germany) and Saarchem (Johannesburg, Gauteng, South Africa) respectively. Carbopol 974P NF was acquired from Noveon, Inc, (Cleveland, Ohio, USA). Ethylcellulose (Ethocel®10), was obtained from Protea Industrial Chemicals (Pty) Ltd (VVadesville, South Africa). Hydroxyethylcellulose (HHX250Pharm) was purchased from Hercules, Aqualon (Germany). Pectin CU701 (low methoxy pectin with the degree of methoxylation in the range ~30-40%) was purchased from Hersbstreith and Fox KG (Pektin-Fabriken, Neuenburg, Germany). Glycine 278 ($M_w$=75.07 g/moL), zinc sulphate ($M_w$=287.54 g/moL) (Rochelle Chemicals, Johannesburg, South Africa), barium chloride ($M_w$=244.28 g/moL) (Saarchem, Pty. Ltd, Unilab, Wadeville, South Africa), calcium sulphate ($M_w$=219.08 g/moL) (Saarchem, (Pty) Ltd. Unilab, Wadeville, South Africa), and liquid paraffin (mineral oil), as a lubricant, was purchased from Rochelle Chemicals (Johannesburg, South Africa). For the preparation of simulated saliva, disodium hydrogen phosphate ($M_w$=141.96 g/moL) was purchased from Rochelle Chemicals (Johannesburg, South Africa), sodium chloride ($M_w$=58.44 g/moL) (LabChem (Pty) Ltd., Edenvale, South Africa), and potassium phosphate monobasic ($M_w$=136.09 g/moL) was purchased from Riedel-de Haen (Seelze, Germany). All other reagents utilized were of analytical grade and used as received. The typical function of the various components of the composite matrix is listed in Table 1.

TABLE 1

Examples of the function of each formulation variable component of the dosage form

| Component | Function |
| --- | --- |
| Chitosan (CHTS) | Permeation enhancer |
| Menthol (MTH) | Flavouring agent and permeation enhancement |
| Gelatine (GEL) | Binding and bioadhesive agent |
| Polyvinyl alcohol (PVA) | Blend stabilizer and matrix stiffener |
| Magnesium Stearate (MS) | Plasticizer and matrix stiffener |
| Sorbitan ester 80 (SP 80) | Facilitates interphase miscibility and permeation enhancer |
| Ethanol (EtOH) | Hydrophobic solute dispersant and pore forming agent |
| Carbopol 974P NF (CARB) | Bioadhesive agent |
| Ethylcellulose 10 (ETH) | Matrix stiffener |
| Hydroxyethylcellulose (HEC) | Homogeneous blend stabilizer |
| Deionized water (DW) | Hydrophilic solute dispersant and pore forming agent |

Preparation of the Multi-Configured Dosage Form

Stock solutions of chitosan and model drug diphenhydramine-loaded cellulosic polymer were homogenously combined in a 2:1 ratio, transferred into pre-oiled moulds and frozen for 24 hours. Formulations were then lyophilized with a freeze phase set at −60° C. for 2 hours and a drying phase at a pressure of 25 mtorr for 48 hours (FIG. 1).

Preparation of the dosage form in accordance with a Box-Behnken experimental design Fifteen formulations were prepared using various combinations of independent variables by the processes of interphase homogenization and lyophilization guided through a two-level, three factor Box-Behnken quadratic design using Minitab Statistical Software, Version 14 (Minitab Inc., State College, Pa., USA). Three categories of independent variables were employed in fabricating the P-ECMs based on statistically generated Box-Behnken design template and these included:
(i) Aqua-based co-particulate dispersion (ACD) composed of PVA, HEC, CARB, GEL and DW
(ii) Ethanol-based co-particulate dispersion (ECD) made up of ETH, MS, MTH, CHTS and EtOH
(iii) Sorbitan ester 80 (SP 80) only Tables 2 and 3 show the two levels of the independent variables used in the design and the experimental design template for the 3 factors, 3 centre points and 15 experimental runs respectively. The lower and upper limits for the factors were set based on their ability to form stable, robust drug loaded formulations using minimal quantities of the components. The formulations were produced using various quantities of ACD, ECB and SP 80 by the process referred to as interphase homogenization. The solutes, ACD and ECD were separately dispersed in two polar protic solvents namely water and ethanol respectively. The two dispersions were mixed together and specific quantities of SP 80 were used to reduce the surface tension of the solutes and solvents. This approach was employed to enable the formation of homogenous and stable co-particulate blend. Overall, the formation of the homogenous blend was aided with a laboratory scale homogenizer (Polytron® 2000, Kinematica AG, Switzerland) for 10 minutes. The resulting stable homogenous blend was then cured for 30 minutes in the dark to enhance solute-solvent intermolecular interactions to occur. For each formulations, 1.0 mL of the blend produced was pipetted into specialized, polystyrene moulds (10 mm diameter by 10 mm height) to give about 20 to 40 matrices for each formulation. These moulds were lightly pre-oiled with inert liquid paraffin to ensure that the matrices do not stick to the moulds. After filling well of the mould with the co-particulate blend, they were pre-frozen at −72° C. over 24 hours and after which they were subjected to lyophilization (freeze-drying) by placing them into a freeze dryer (Bench Top 2K, Virtis, New York, USA) set at −50° C. and 0.42 mBar for 48 hours. After lyophilization, produced formulations were stored away for further testing in closed glass jar with active silica-containing desiccant bags. Depending on the solubility of the model drug, a specific quantity of either hydrophilic or hydrophobic drug is dispersed in the aqueous (ACD) or alcoholic (ECD) compartment respectively. The model drug employed for this stage was phenytoin sodium.

TABLE 2

Levels of the independent variables employed in the Box-Behnken design

| Independent Variables | Levels | | Units |
| --- | --- | --- | --- |
| | Low | High | |
| $ACD^a$ | 0 | 2 | mg |
| $ECD^b$ | 3 | 5 | mg |
| $SP\ 80^c$ | 0.3 | 0.7 | mL |

$^a$Aqua-based co-particulate dispersion;
$^b$Ethanol-based co-particulate dispersion;
$^c$Sorbitan ester 80
Note:
For ACD:
0 - PVA (650 mg) + HEC (350 mg) + GEL (400 mg) + CARB974 (100 mg) + DW (30 mL),
1 - PVA (475 mg) + HEC (525 mg) + GEL (350 mg) + CARB974 (150 mg) + DW (20 mL), and
2 - PVA (300 mg) + HEC (700 mg) + GEL (300 mg) + CARB974 (200 mg) + DW (25 mL).
For ECD:
3 - CHTS (550 mg) + MS (350 mg) + MTH (200 mg) + ETH 10 (400 mg) + EtOH (10 mL),
4 - CHTS (425 mg) + MS (325 mg) + MTH (250 mg) + ETH 10 (500 mg) + EtOH (13 mL),
5 - CHTS (300 mg) + MS (300 mg) + MTH (300 mg) + ETH 10 (600 mg) + EtOH (15 mL)

TABLE 3

Box-Behnken template for the preparation of the pore regulated matrices

| Formulation | Composition | | |
| --- | --- | --- | --- |
| | $ACD\ (mg)^a$ | $ECD\ (mg)^b$ | $SP\ 80\ (mL)^c$ |
| 1 | 0 | 3 | 0.5 |
| 2 | 0 | 5 | 0.5 |
| 3* | 1 | 4 | 0.5 |
| 4 | 0 | 4 | 0.7 |
| 5* | 1 | 4 | 0.5 |
| 6 | 1 | 5 | 0.3 |
| 7 | 1 | 3 | 0.7 |

TABLE 3-continued

Box-Behnken template for the preparation of the pore regulated matrices

| Formulation | Composition | | |
|---|---|---|---|
| | ACD (mg)[a] | ECD (mg)[b] | SP 80 (mL)[c] |
| 8 | 2 | 5 | 0.5 |
| 9 | 1 | 5 | 0.7 |
| 10 | 2 | 4 | 0.3 |
| 11* | 1 | 4 | 0.5 |
| 12 | 2 | 3 | 0.5 |
| 13 | 2 | 4 | 0.7 |
| 14 | 1 | 3 | 0.3 |
| 15 | 0 | 4 | 0.3 |

[a]Aqua-based co-particulate dispersion;
[b]Ethanol-based co-particulate dispersion;
[c]Sorbitan ester 80;
*The three experimental design template centre points Preparation of the Crosslinked Multi-Configured Pharmaceutical Dosage Form A 3% w/v solution of pectin was used to dissolve 40 mg/mL of model drug DPH. Glycine (0.6% w/v) was employed as a collapse protectant. This solution (1 mL) was pipetted into custom moulds lubricated with mineral oil. Mineral oil was the lubricant of choice as it has no effect on the taste of the final product as well as imparting minimal hydrophobicity. Preparing pre-lyophilized crosslinked systems involved adding 0.5 mL of various salt solutions to the 1 mL of pectin and DPH solution in the moulds to effect crosslinking of the pectin. The salt solutions comprised of either zinc sulphate, barium chloride, or calcium sulphate, formulated as individual 4% w/v solutions. These dosage forms were therefore formulated on a 1:0.75 ratio of crosslinker to polymer. The crosslinked systems were allowed to cure for 24 hours at 25° C. in a dark cupboard, and thereafter stored in a −70° C. freezer (Sanyo Ultra Low Temperature Freezer, Sanyo Electric Co. Ltd, Japan model) for 24 hours prior to lyophilization (Labconco Freeze Dry Systems, Labconco Corporation, Kansas City, Mo., US). The system then subjected to lyophilization for 36 hours. Preparation of the post-lyophilized crosslinked system involved adding 2 mL of the polymer-DPH solution into the lubricated plastic moulds and stored in a −70° C. freezer for 24 hours. The resultant systems were then subject to lyophilization for 24 hours. Upon lyophilization, the pharmaceutical dosage forms were crosslinked with 0.5 mL of the various salt solutions and allowed to cure for 1 hour at 25° C. in a dark cupboard. They were then subjected to further lyophilization for 24 hours. A few were prepared by crosslinking both before and after the lyophilization process and were formulated in a 2:1.5 ratio of crosslinker to polymer. To assess the influence of the type of crosslinker and the method of crosslinking (i.e. before or after lyophilization) on the overall release of the drug from the system various formulations were produced. The various formulations that were evaluated are listed in Table 4.

TABLE 4

Examples of the composition of the crosslinked formulations

| Formulation | Crosslinker | | | Method of Crosslinking | |
|---|---|---|---|---|---|
| | CaSO$_4$ | BaCl$_2$ | ZnSO$_4$ | Pre-lyophilized | Post-lyophilized |
| Un-crosslinked formulation | No | No | No | No | No |
| Ca-crosslinked pre-lyophilized | Yes | No | No | Yes | No |
| Ca-crosslinked post-lyophilized | Yes | No | No | No | Yes |
| Ca-crosslinked pre- and post-lyophilized | Yes | No | No | Yes | Yes |
| Ba-crosslinked pre-lyophilized | No | Yes | No | Yes | No |
| Ba-crosslinked post-lyophilized | No | Yes | No | No | Yes |
| Ba-crosslinked pre- and post-lyophilized | No | Yes | No | Yes | Yes |
| Zn-crosslinked pre-lyophilized | No | No | Yes | Yes | No |
| Zn-crosslinked post-lyophilized | No | No | Yes | No | Yes |
| Zn-cross-linked pre- and post-lyophilized | No | No | Yes | Yes | Yes |

Determination of Final Mass of the Formulations

The final dry mass, after lyophilization, of the fifteen matrices were measured using the laboratory scale weighing balance (Mettler Toledo, AB104-S, Microsep Pty Ltd, Switzerland). This was carried out to generate data that can be employed to generate the eventual mass of the formulation.

Evaluating the Disintegration Behavior of the Formulations

Disintegration of the formulations was conducted using a method specific to rapidly disintegrating solid oral dosage forms adapted from a comprehensive literature review. A Texture Analyzer (Stable Micro Systems, Surrey, UK) with a flat, cylindrical probe was used to mimic the influence that the tongue has on the disintegration of the delivery system. Individual formulations were pre-weighed and attached to the abovementioned probe. A petri-dish containing 5 mL of simulated saliva (pH 6.75) heated to 37° C. was used. The probe with attached matrix was then lowered into the petri-dish at a pre-determined force for 60 seconds. The resulting distance-time profile generated was used to determine the onset of disintegration, disintegration rate, and penetration distance of the probe through the matrix.

Evaluating the Drug Release Behavior of the Formulations

Each pore regulated matrix was immersed into 25 mL of simulated saliva (Table 5; pH 6.8) contained in closed 100 mL capacity glass jars. For studies at the specified condition, three replicate samples of the matrices were maintained at 37±0.5° C. and 20 rpm in a shaking incubator (Orbital Shaker Incubator, LM-530, Lasec Scientific Equipment, Johannesburg, South Africa). A 3 mL filtered dissolution sample was withdrawn at specific time intervals (30, 60, 120, 240, 360 and 480 minutes) over 8 hours and sink conditions maintained by replacing withdrawn volume with fresh simulated saliva at each sampling time. The amount of drug released was determined by the Ultraviolet Spectroscopy (Specord 40, Analytik Jena, AG, Germany) at $\lambda_{max}$=206 nm. All experiment was carried out in triplicate.

TABLE 5

Composition of simulated saliva (Per and Wong, 1999)

| Constituents | Simulated Saliva | Simulated Plasma |
| --- | --- | --- |
| Disodium hydrogen phosphate (Na$_2$HPO$_4$) | 2.380 g | 0.795 g |
| Potassium dihydrogen phosphate (KH$_2$PO$_4$) | 0.190 g | 0.144 g |
| Sodium chloride (NaCl) | 8.000 g | 9.000 g |
| Phosphoric acid (H$_3$PO$_4$) | 0.300 mL | — |
| Deionized water | 1000 mL (1 L) | 1000 mL (1 L) |

Analysis of Matrix Physicomechanical Strength

Textural analysis of the formulations was conducted using a Texture Analyzer (Stable Microsystems, Surrey, UK) to determine changes in the stress-strain parameters, such as the yield-modulus, polymeric fracture, and resilience behaviour. Unhydrated samples were investigated, since any form of hydration resulted in disintegration of the matrix. Force-distance or force-time profiles are adequate to perform the calculations necessary for the above. Tests included matrix resilience ($M_R$), energy of matrix distortion ($C_D$) and the matrix firmness ($M_F$). A calibrated Texture Analyzer fitted with a cylindrical steel probe (50 mm diameter) was employed for the determination of the matrix resilience while the energy of matrix distortion and matrix firmness were measured using a flat-tipped steel probe (2 mm diameter). For all determinations, the textural settings listed in Table 6 were fixed throughout. Data was captured at a rate of 200 points per second via Texture Exponent Software (Version 3.2) and all determinations were done in triplicate.

TABLE 6

Textural settings employed for the determination of MR, DE and BHN

| | Settings | | |
| --- | --- | --- | --- |
| Parameters | $^aM_R$ | $^bM_F$ | $^c\epsilon_D$ |
| Pre-test speed | 1 mm/sec | 1 mm/sec | 1 mm/sec |
| Test speed | 0.5 mm/sec | 0.5 mm/sec | 0.5 mm/sec |
| Post-test speed | 10 mm/sec | 10 mm/sec | 10 mm/sec |
| Compression force | — | 40N | 40N |
| Trigger type | Auto | Auto | Auto |
| Trigger force | 0.5N | 0.5N | 0.5N |
| Load cell | 5 kg | 5 kg | 5 kg |
| Compression strain | 50% | — | — |

$^a$Matrix resilience;
$^b$Matrix firmness;
$^c$Energy of matrix deformation

Computation of the drug loading and entrapment capacity of the formulations Drug entrapment efficiency (DEE) was conducted by allowing the formulations to completely disintegrate in a 100 mL solution of simulated saliva that was then analyzed via UV Spectroscopy to determine the drug content. DEE was then calculated using Equation 1.

DEE=Actual drug concentration/Theoretical drug concentration×100     Equation 1

Where DEE=Drug entrapment efficiency (%), the Actual and Expected drug concentrations respectively=mg/mL. The expected and actual drug concentrations were calculated using basic mathematical ratios.

The drug loading capacity (DLC) was calculated utilizing Equation 2. This parameter was an indication of the drug loading efficiency of the formulations.

$$\% \, DLC = \frac{A_d}{T_d} \times 100 \qquad \text{Equation 2}$$

Where % DLC=drug loading capacity, $A_d$=actual quantity of drug loaded and $T_d$=theoretical quantity of drug loaded.

For each determination, one formulation was dissolved completely in simulated saliva solution (pH 6.8) with the aid of the laboratory homogenizer (Polytron® 2000, Kinematica AG, Switzerland). 2 mL sample was then manually withdrawn and filtered through a 0.45 µm pore size Cameo Acetate membrane filter (Milipore Co., Bedford, Mass., USA). Appropriate dilutions were performed and samples were then analyzed by ultraviolet spectroscopy (Specord 40, Analytik Jena, AG) at 206 nm (model drug phenytoin sodium). The absorbance values generated were fitted into the linear polynomial equation of the calibration curve for phenytoin sodium (FIG. 2). The outcome of this computation was then put into Equation 2 to generate the % DLC for each formulation. All evaluations were conducted in triplicate.

In Vitro and Ex Vivo Assessment of Bioadhesive Capacity

Bioadhesion was evaluated through the measurement of peak adhesion force and the calculation of work necessary for the adhesion of the formulation to the surface of a membrane using the Textural Analyser. Experimental data was analysed using Texture 32 Exponent. Before initiating contact between the two surfaces, the membrane was moistened with simulated saliva (pH 6.75). A contact force of 0.5N for 10 seconds was applied. The membrane was then moved upwards from the formulation at a constant speed of 0.1 mm/sec, and the peak adhesion force (N) was measured. The work of adhesion (N·mm) was calculated from the area under the force/-curve. Results are reported as the average of three measurements.

The ex vivo bioadhesive strength of the formulations were determined using a calibrated Texture Analyzer (TA.XTplus, Stable Micro Systems, Surrey, UK) fitted with a cylindrical stainless steel probe (10 mm diameter) and freshly isolated porcine buccal mucosa (0.8 mm±0.1 mm thickness) as the model tissue. All measurements were done in three replicate samples. The buccal mucosa was attached to the cylindrical probe while the formulation was mounted onto the texture analyzer stage. The two surfaces were properly aligned to ensure that they came into direct contact with each other during measurements. The settings employed during testing are: contact force (0.1 g), pre-test speed (2 mm/sec), test speed (0.5 mm/sec), post-test speed (10 mm/sec), applied force (102 g or 1N), return distance (8 mm), contact time (10 secs), trigger type (auto) and trigger force (5 g or 0.049N). For each measurement, the surface of the porcine buccal mucosa (for contact with the formulation) was made evenly wet by dipping it into 2 mL of simulated saliva (Table 4) placed in a glass petri dish for 5 minutes. Subsequently, the tissue is lowered towards the formulation to make contact with it. Bioadhesive strength was calculated from the generated force-distance curve as the peak detachment force ($F_{det}$) and work of adhesion ($\omega_{adh}$). The peak detachment force (N) was taken as the maximum force needed for detaching the matrix from the tissue while the work of adhesion (J) was calculated as the area under the Force-Distance curve.

Ex Vivo Permeation Studies Utilizing Porcine Buccal Mucosa

The porcine buccal mucosa was obtained from the cheek region of freshly slaughtered domestic pigs from a regional abattoir (Mintko Meat Packers, Krugersdorp, South Africa). After collecting the mucosal specimens, they were immediately transported in a refrigerated transport box and transferred to our in vivo laboratory within 1 hour. The pig's buccal mucosa was specifically selected for this study because they have non-keratinized buccal mucosa similar to that of human beings. In fact, the oral mucosa of pigs resembles that of humans more closely than any other animal in terms of structure and composition (Shojael et al., 2001; Sudhakar et al., 2006). Excess connective and adipose tissues were trimmed away (using surgical scalpel and scissors) from the mucosal specimens. The average porcine buccal mucosal thickness employed throughout the study was 0.8±0.1 mm. This was measured using a manually operated Vernier caliper (25×0.01 mm capacity, Germany). Subsequently, the trimmed specimens were snap frozen in liquid nitrogen and stored at −70° C. for up to 2 months. Researchers have reported that freezing tissue specimens (either snap freezing with liquid nitrogen or the standard freezer) does not change their diffusion or permeation behavior when used for such studies (Van der BijI et al., 1998; Van Eyk and Thompson, 1998; Van Eyk and Van der Bijl, 2004; Consuelo et al., 2005; Giannola et al., 2007).

Preparation of Tissue and Permeation Studies

Before conducting each experiment, the frozen mucosal specimens were thawed and equilibrated (re-hydration to regain elasticity lost when frozen) for 2 hours in 100 mL phosphate buffered saline (PBS, pH 7.4) at room temperature (20±0.5° C.). The PBS solution was changed every 30 minutes with a fresh solution. After re-hydration, mucosal disks (15 mm in diameter, area of 2.27 cm$^2$) were cut using surgical scissors from the harvested specimen and mounted in the flow through Franz type diffusion cells (Permegear, Arnie Systems, USA) connected to an heat circulating water bath/heating system. The receiver compartment contained 10 mL simulated plasma, pH 7.4 (Table 4) while the donor compartment contained a 2 mL solution of the drug-loaded formulation in simulated saliva. Uniform mixing within the receiver compartment was achieved by magnetic stirring. Permeation studies were conducted in triplicate for each formulation at 37±0.5° C. At pre-determined time intervals over 480 minutes (30, 60, 120, 240, 360, 480 minutes), 2 mL sample volume was withdrawn from the receiver compartment of each cell and replaced with the same volume of fresh simulated plasma. At the end of each experiment, the cells were disinfected with sodium hypochlorite and 70% ethanol solution and then allowed to dry out, ready for the next study.

Assay Development

Withdrawn samples were assayed for phenytoin sodium at 206 nm using a UV-Vis spectrophotometer (Cecil CE 3021, 3000 Series, Cecil Instruments, Cambridge, England). The calibration curve for phenytoin sodium in simulated plasma is illustrated in FIG. 3.

The drug flux values ($J_s$) through the membrane were calculated at the steady state per unit area by linear regression analysis of permeation data following Equation 3 (Giannola et al., 2007).

$$J_s = \frac{Q_r}{A \times t} \quad \text{Equation 3}$$

Where $J_s$ is the drug flux (mg cm$^{-2}$ min$^{-1}$) $Q_r$ is the amount of phenytoin sodium that passed through the porcine buccal mucosa into the receptor compartment (mg), A is the active cross-sectional area accessible for diffusion (cm$^2$) and t is the time of exposure in minutes.

Rheological Investigations of the Homogenous Co-Particulate Blends

Samples of the monolayered system were hydrated with 5 mL of simulated saliva and analyzed using a Modulated Advanced Rheometer system at 37° C. The rheological characteristics in terms of viscosity ($\eta$) and deformation ($\gamma$) of the un-lyophilized blends used in preparing the matrices and its overall influence on porous matrix integrity was investigated using the Modular Advanced Rheometer System equipped with the Haake Rheowin data and job software (Haake Mars, Thermo Scientific, Waltham, Mass., USA). The rheometer stage was filled with 1.5 mL of sample (blend) for each formulation. The rotor C35/1° Titan sensor type was employed. Rheological measurement parameters were fixed at an operational temperature of 25° C., analytical contact time of 180 secs, controlled rate ranging between 0 secs$^{-1}$ to 5 secs$^{-1}$ and constant shear rate of 0 secs$^{-1}$ to 500 secs$^{-1}$. Mean viscosity ($\eta$) and deformation ($\gamma$) values were computed at an average, constant shear rate of 250 secs$^{-1}$.

Surface Morphological Characterization of the Formulations

The nature and architecture of the porous surface morphology of the formulations was viewed and characterized using Scanning Electron Microscopy (SEM). Samples (12 mm diameter×4 mm thickness) were sputter-coated with gold-palladium and viewed four times from different angles under a JSM-840 Scanning Electron Microscope (JEOL 840, Tokyo, Japan) at a voltage of 20 keV and a magnification of 1000×.

Qualitative Evaluation of Matrix Porosity

An inverse relationship exists between porosity and density with an elevation in density being an indication of low porosity (Dourdain, et al., 2006). The porosities (ø) of the matrices were computed from the true and apparent densities of the formulations using volume and weight measurements. The mathematical expression used is stated in Equation 4.

$$\text{Porosity} = \frac{\rho_{bulk} - \rho_{apparent}}{\rho_{bulk}} \times 100 \quad \text{Equation 4}$$

The apparent ($\rho_{apparent}$) and bulk ($\rho_{bulk}$) densities were calculated using the mass and volume measurements of the dry and hydrated matrices respectively. The weights and dimensions of the samples were recorded using a weighing balance (Mettler Toledo, AB104-S, Microsep Pty Ltd, Switzerland) and a manually operated vernier caliper (25×0.01 mm capacity, Germany) respectively. Also the parameters for computing the bulk density were measured 30 minutes post hydration because at this time point, all the formulations had attained a constant weight increment and the process of matrix loss had not yet commenced. All measurements were done in triplicate.

Quantitative Porosimetric Analysis of the Matrices

Porosimetry is an analytical technique used to determine various quantifiable aspects of a material's porous nature such as total pore volume, surface area and average pore diameter which provides information about pore types. These parameters were detected in duplicate using the surface area and porosity analyzer equipped with the ASAP 2020 V3.01 software (Micromeritics, ASAP 2020, Norcross, Ga., USA). A dry sample weight of 100 mg was employed for all 15 formulations. The porosimetric investigations were conducted in two phases namely degassing and analysis stages. Samples were subjected to degassing to remove air, gases and other adsorbed species from the sample surface. The operating settings employed included temperature ramp rate (10° C./minutes), target temperature (90° C.), evacuation rate (50 mmHg/seconds), unrestricted evacuation (30 mmHg), vacuum set point (500 pmHg), evacuation time (60 minutes), heating hold temperature (120° C.), hold time (900 minutes), evacuation and heating hold pressure (100 mmHg) and analysis time (400 minutes).

Elucidation of Possible Structural Transformations During Preparation

Infrared spectra were recorded on the Bruker Optic FTIR Spectrometer (Tensor 27 Spectrometer, Bruker Optics Inc. Billerica, Mass., USA) equipped with Opus Version 6.0 software. 10 mg of sample for the respective formulations was placed on the sample holder on the machine stage. Blank scans (background spectra) were taken before placing the sample for analysis. Samples were analyzed at wavenumbers ranging from 4000-400 $cm^{-1}$, scan time=32 scans and resolution=4 $cm^{-1}$.

Results and Discussion

The layering effect of the pharmaceutical dosage form Chitosan possesses OH and $NH_2$ groups that can give rise to hydrogen bonding and the linear molecule expresses a sufficient chain flexibility, the conformation of which is highly dependent on ionic strength. In addition, the cationic nature of chitosan results with a strong electrostatic interaction with mucus or a negatively charged mucosal surface[21-22]. Stock solutions of equal concentrations of HPC and chitosan, both mixed in distilled water, were prepared. The solutions were combined in a 2:1 ratio of chitosan:HPC under constant stirring to prepare a suspension. This suspension was frozen for 24 hours and subsequently lyophilized for 48 hours. The resulting formulations were seen to have two distinct layers: a pale, porous upper layer, and a darker, granular lower layer. This layering effect can be attributed to a number of reasons. Despite being made in the same concentrations, the HPC solution is more viscous than chitosan. Therefore, the chitosan particles were suspended in the HPC solution upon mixing. During the freezing process, the denser chitosan particles settled to the bottom of the mould under the influence of gravity. The density of chitosan is approximately 1.35-1.40 $g/cm^3$ as opposed to the 0.5 $g/cm^3$ displayed by HPC. Also contributing to the layering effect is the lyophilization process itself. Lyophilization involves the removal of water from a frozen product by sublimation (sublimation is the process whereby frozen liquid goes directly to the gaseous state without passing through the liquid phase). The potentially important phases during this process in relation to the layering effect between chitosan and HPC are the pre-freezing and primary dying phases respectively.

Influence of the Pre-Freezing Step

Since lyophilization is the change in state from the solid to the gaseous phase, the product must be properly pre-frozen. When an aqueous suspension is cooled, changes occur in the concentration of solute of the product matrix. As cooling proceeds, water is separated from the solute as it changes to ice, creating more concentrated areas of solute. These pockets of concentrated materials have a lower freezing temperature than the surrounding water.

Influence of Primary Drying

Molecules migrate from the higher pressure sample to a lower pressure area. The vapor pressure of the product forces sublimation of the water vapor from the frozen product matrix to the collector. Kinetic energy is not evenly distributed among molecules; some molecules have greater energy and thus higher velocities than others at any moment. When a liquid is placed in an evacuated container at a constant temperature, the molecules with the highest energies break away from the surface of the liquid and pass into the gaseous state, and some of the molecules subsequently return to the liquid, or condense. When the rate of condensation equals the rate of vaporization at a definite temperature, the vapor becomes saturated and a dynamic equilibrium is established. The pressure of the saturated vapor above the liquid is then known as the equilibrium vapor pressure. Vapor pressure serves as a quantitative expression of the escaping tendency of molecules. Taking these facts into account, it is possible that water vapor is drawn quicker from chitosan due to its higher vapor pressure, further influencing the formation of the lower layer. Water vapor is drawn at a slower rate from the more viscous and less dense HPC layer, resulting in the formation of the upper layer of the system. The layering effect occurs as a result of density differences between the unsolubilized chitosan and respective polymer solutions. Hydrophobicity and hydrophilicity could play a role in the layering phenomena. As the hydrophilic polymer solution separates from the hydrophobic unsolubilized chitosan. The layering phenomenon could also be attributed to the phase separation because of thermodynamic incompatibilities of the polymer solutions. When Gibbs free energy is negative miscibility of the polymer solution is enhanced[23]. Chemistry of the polymers play an integral role as hydrogen bonding, ion-ion pairing favours the mixing enthalpy and the polymer components mix completely forming a homogenous solution prior to lyophilisation which results in the formation of a mono-layered matrix[23]. Hydrophilic polymers usually have a combination of proton donating and proton accepting groups which are expected to enhance miscibility[23]. The presence of water in these formulations is postulated to enhance miscibility through the formation of polymer-water-polymer associates. The higher than anticipated matrix resilience displayed can be attributed to the chitosan component of the WDS imparting increased rigidity to the matrix. Despite the chitosan component of the WDS displaying a greater ability to withstand stress, its ability to disintegrate more rapidly than the cellulose component can be attributed to its granular, compacted state in its lyophilized form. Contact with fluid results in swelling of these chitosan grains, displacing the surrounding granules that results in increased spaces for fluid to penetrate, thus enhancing disintegration.

Mass Variability of the Matrices

Generally, formulations appeared as whitish, compact platforms with a diameter of 8 mm and thickness of 5 mm. Also, the matrices presented with convex-shaped base and a flat surface. Overall the matrices can be described as relatively light weighted with values ranging from lowest (121.95±0.95 mg) to highest (133.75±0.35 mg). An average weight of 128.44±3.49 mg for all the 15 formulations was obtained as well. The presence of pores within the matrices may contribute to their low weight as their density is also reduced. The differences (R=0.459) in the weights of the 15 formulations may be attributable to the differences quantities of the components of each formulation. As regards intra-formulation weight differences, a close relationship (R=0.961) existed amongst matrices prepared from the same formulation. This implies that interphase, co-particulate, co-solvent, homogenization technique of preparing the P-ECMs employed in this investigation was efficient and produced a homogenous blend which minimized disparities within the same formulation batch. The average weights of the formulations are presented in FIG. 4.

Formulations produced revealed multi-configured polymeric structures. Disintegration rate was assessed according to the methods outlined by El-Arini et al. The distance-time profiles generated exhibit three characteristic regions: an initial region (IR) where the dosage form resists the force applied by the probe before disintegration starts, an ascending region (AR) where the dosage form disintegrates as the probe distance increases sharply in search of the target force, and the plateau region (PR) that indicates when disintegration is complete.
1. Onset of Disintegration—determined by the projection on the time axis of the intercept of the slope of the IR with the slope of the AR of the disintegration profile.
2. Disintegration Rate—slope of the AR on disintegration profile.
3. Penetration Distance—maximum distance traveled by the probe into the dosage form.

The average disintegration time for the total system was 28.96 seconds. The average disintegration rate of the system was seen to be 0.1457 mm/sec with onset of disintegration being almost instantaneous (FIG. 5). This almost instantaneous disintegration is as a result of the highly porous nature of the matrix. The use of highly hydrophilic polymers further increased fluid penetration into the matrix. Although the monolayered matrix did not disperse immediately upon contact with simulated saliva, an opaque gel-like substance though to be as a result of polyacrylic acid (PAA) was observed. The gel has the dual role of imparting bioadhesivity and enhanced permeation to the formulation, allowing for improved drug absorption by increasing contact time and surface area with the transmucosal membrane, thus facilitating drug penetration. The figure below is a representation of the total disintegration rate of a portion of the samples produced. Sample 4 represents the average disintegration rate.

The aforementioned gel resulting from disintegration of the monolayered system displayed a relatively high initial viscosity that decreased sharply when shear rate exceeded 100 s$^{-1}$. Shear stress was seen to initially spike with the increasing shear rate and time. This is of importance since it is the gel that will ultimately adhere to the oral mucosa and release drug into the circulation. The highly viscous nature of this gel coupled with its ability to withstand a relatively high shear rate further demonstrates its ability to remain undisturbed in the oral cavity, ultimately allowing for constant drug release.

In Vitro Drug Release from the Matrices

Diverse release patterns were observed for the 15 formulations which may be associated with the various degrees of co-particulate dispersion, interphase homogenization polymerization, solute-solvent interaction and lyophilization due to the differences in the quantities of the formulation constituents. FIG. 4 illustrates the drug release trends of the 15 formulations. The diverse dissolution patterns displayed by the 15 formulations were analysed and substantiated by the time-point approach referred to as mean dissolution time (MDT). The application of the MDT provides a more accurate view of the drug release behaviour as it is determined as the sum of the individual periods of time during which a specific fraction of the total drug dose is released (Pillay and Fassihi, 1998; Rinaki et al., 2003; Ansari et al., 2004). Equation 5 was employed in the calculation of the MDT.

$$MDT = \sum_{i=1}^{n} t_i \frac{M_t}{M_\infty}$$  Equation 5

Where $M_t$ is the fraction of dose released in time $t_i$, $t_i = (t_i + t_{i-1})/2$ and $M_\infty$ corresponds to the loading dose.

The MDT$_{50\%}$ data point was selected for the 15 formulations as this was applicable to all generated profiles (FIG. 6). The MDT$_{50\%}$ numerical values are stated in Table 7. Low MDT$_{50\%}$ and high MDT$_{50\%}$ values represent rapid or prolonged drug release patterns respectively.

TABLE 7

MDT$_{50\%}$ values showing the drug release characteristics of the formulations

| Formulation | MDT$_{50\%}$ (minutes) |
| --- | --- |
| 1 | 104.00 |
| 2 | 85.00 |
| 3 | 98.00 |
| 4 | 105.00 |
| 5 | 104.50 |
| 6 | 220.00 |
| 7 | 225.00 |
| 8 | 88.50 |
| 9 | 15.00 |
| 10 | 185.00 |
| 11 | 100.00 |
| 12 | 210.00 |
| 13 | 90.00 |
| 14 | 161.00 |
| 15 | 22.50 |

All the 15 formulations elicited a level of burst release of drug at $t_{30 minutes}$ and this may be attributable to their porous structure (FIG. 6). The initial relatively quick release is followed by a moderately consistent amount of drug released per unit time. The observed trend is of advantage to the intended application of this drug delivery matrix as the burst release initiates the pharmacological action which is sustained by the consistent release of drug molecules over time. The porous matrix has demonstrated the potential for application as a controlled release system over 8 hours. Generally, formulations comprised of higher levels of hydrophobic solutes (Formulations 7, 6, 12) dispersed in ethanol than the hydrophilic components displayed a more controlled release pattern while the reverse also applies to (Formulations 9, 15, 2). Also, the quantity of the pore-forming agents, water and ethanol influenced drug release as formulations with the highest level of ethanol (15 mL) displayed quicker release rates (Formulations 2, 8, 9) than those with highest amounts of water (25 mL) (Formulation 8, 10, 12 and 13). An exception to this trend is formulation 4 which displayed slower release rates (MDT$_{50}\%=220$ minutes) despite the high level of ethanol employed in its preparation that may be due to inclusion of a low amount of hydrophilic span 80 (Table 3).

The various crosslinked formulations demonstrated diverse release behavior: 45-92% of the total drug was released from the systems after 1 hour (FIG. 7a-c). On comparison of the release profiles, non-crosslinked pectin formulations showed a comparatively lower propensity to modulate release of the hydrophilic drug and 82% of the drug was released after 30 minutes (FIG. 7a). Formulations that included a crosslinking step showed a more prolonged release of drug. When comparing the pre-lyophilized crosslinked pectin formulations, calcium crosslinking demonstrated superior control over the release of drug than the zinc or barium, with barium exerting the least control over drug release (FIG. 7a). With regards to the post-lyophilized crosslinked pectin, calcium crosslinking once again affected enhanced control over drug release than either zinc or barium (FIG. 7b). This is attributed to the enhanced propensity of calcium cations to establish thermodynamically stable intermolecular crosslinks to form a tight-knit structure which effectively entraps the incorporated drug. Pectin formulations which were crosslinked both before and after the lyophilization process yielded different release profiles as compared to formulations subjected to a single crosslinking step (FIG. 7c). Here, application of barium-crosslinking to the formulation matrix controlled the release of drug to a greater extent than either zinc- or calcium-crosslinking, with calcium-crosslinking showing the least control. Thus, depending on when lyophilization of the formulations occurred, the pectin molecules were exposed to variable crystal formation-precipitation-sublimation cycles, thus the arrangement of the pectin molecules in space differed, ultimately affecting the manner in which the crosslinking cations were able to establish inter- and intramolecular crosslinks. The lyophilized crosslinked formulations maintained their integrity for the duration of release study (3 hours) compared to that of the non-crosslinked pectin formulation, which demonstrated signs of disintegration, indicative of the propensity of the metal cations to establish and maintain an interconnected polymeric network structure.

Elucidation of Rheoloqical Behaviour of the Homogenous co-particulate Blends Viscosity can be describec b) a parameter that quantifies the resistance of the fluid homogenous blends to flow when an external force is applied. The behaviour of the homogenous blends for the 15 formulation can be described as Non-Newtonian because their viscosity magnitudes were dependent upon shear conditions (i.e. shear rate and shear stress). In other words, they can be described as fluids that cannot be described by a single constant viscosity as this change with applied shear stress and shear rate. With reference to the blends, an increase in shear stress and shear rate results in a decrease in viscosity values. FIGS. 8A and 8B represent a typical profile showing the relationship between viscosity, shear rate and shear stress for the homogenous blends. The mean viscosity values ($\eta$) computed at a constant shear rate for the 15 formulations differed with values ranging from $0.7893 \times 10^4 \pm 0.0007 \times 10^4$ Pa·s to $8.6580 \times 10^4 \pm 0.002 \times 10^4$ Pa sparing the viscosity with the surface morphology of the matrices, informing features were noted. The viscosity values were classified as low ($<1.05 \times 10^4$ Pa·s), intermediate ($>1.05 \times 10^4$ Pa·s$<4 \times 10^4$ Pa·s) and high ($>5 \times 10^4$ Pa·s$<9 \times 10^4$ Pa·s) as this was a systematic approach of interpreting this set of data.

The lowest range of viscosity values ($<1.05 \times 10^4$ Pa·s) were recorded for Formulations 1, 4, 9 and 13 (FIG. 6a, d, i and m) presented with irregular pore structure connected with spongy/fluffy barriers (interconnections). Formulation 13 had lower expanse of fluffy surface morphology as compared with the others in this class and this may be attributable to its higher viscosity value. Formulations 6, 7, 8, 10, 12 and 13 had the intermediate viscosity values ($>1.05 \times 10^4$ Pa·s$<4 \times 10^4$ Pa·s) and generally they displayed pore structures with asymmetrical dimensions and rigid/dense interconnections (FIGS. 6f, g, j and l) with the exclusion of Formulation 8. Formulations 2, 5, 3, 11, 14 and 15 generated the high viscosity magnitudes ($>5 \times 10^4$ Pa·s$<9 \times 10^4$ Pa·s) and their surfaces were characterized with circular pore structures with a high volume of distribution and web-like, low density interconnections. An exception to this trend was Formulation 14. An illustration of the different viscosity values are presented in FIG. 9. Overall, it can be proposed that viscosity may have an effect on the process of freezing and sublimation of frozen solvent (conversion from solid to gas) to create the intra-matrix porous structure (includes pore geometry, interconnections, pore width and pore volume of distribution) during lyophilization. The solvent flow properties are interfered with by the solute co-particulates present in the homogenous blend.

Deformation ($\gamma$) can be described as the change in internal structure of the homogenous blend due to an applied compressive external force. The 15 formulation homogenous blends displayed constant deformation magnitudes (FIG. 10). The outcome of this test suggests that the blends are robust and stable to externally exerted force. Also, this may be indicative of the absence of irreversibly chemical interactions or transformations amongst components during the processes (homogenization and lyophilization) of preparing the matrices. In other words, the method of preparing the matrices can be described as a physical interaction which does not irreversibly alter the chemical backbone structure of the components as well as their individual contributive properties which enhance the overall efficiency of the formulations to suit their intended application.

Quantitative Porosimetric Analysis of the Matrices

Porosity analysis quantified total pore volume, surface area, average pore diameter and pore interconnection quotient. This investigation enumerated the findings depicted by the generated SEM micrographs (FIG. 20) of each formulation as well as the qualitative porosity measurement (FIG. 9). Average pore diameter ranged between 40Å and 100Å with cumulative pore volume as a measure of pore distribution with values of $6.5 \times 10^{-4}$ cm$^3$/g and $9.5 \times 10^{-3}$ cm$^3$/g while the cumulative surface area spanned over 28 cm$^2$/g to 800 cm$^2$/g. The above-mentioned numerical measures demonstrate that the performance of the P-ECM is highly dependent on the pore structure, diameter, the volume of pore distribution which also signifies the integrity and configuration of the interconnections as well as the surface area. These parameters vary for each formulation and this is observed to have a significant impact on their physicochemical and physicomechanical qualities. FIGS. 11, 12 and 13 respectively depict the average pore diameter, cumulative pore volume and surface area measured for the 15 experimental design formulations. The range of pore sizes indicated that the 15 formulations were mesoporous in nature because their diameters are between 20Å to 500Å.

Textural Profile Analysis for Elucidation of the Physicomechanical Properties of the Pharmaceutical Dosage Form Anchors 1 and 2 on the Force-Distance and Force-Time profiles (FIGS. 16 and 17) are representative of the cellulose component of the formulation with anchors 2 and 3 representing the chitosan component. Anchors 3 and 4 correspond to the formulation as a whole. The average matrix yield and tolerance values of the cellulose layers (0.447N/mm; 1.965N.mm respectively) were lower than that of the chitosan layer (0.859N/mm; 7.198N.mm respectively) due to its highly porous nature.

The physicomechanical parameters measured for the 15 formulations were matrix resilience ($M_R$), energy of matrix distortion ($\epsilon_D$) and the matrix firmness ($M_F$) (Table 6). The matrix resilience can be described as the elastic cohesiveness of the matrices that is the capability to recover to their original dimensions post the application of an external compressive strain. Matrix firmness is a measure of the force required to attain a given deformation of a body while the energy of distortion is the work performed (or energy dissipated) in Joules to overcome the adhesive and cohesive forces within the material. These parameters are measures of matrix integrity and robustness such that an elevated matrix resilience, firmness and reduced energy of distortion values indicate high matrix strength. With respect to the outcome of this study, a direct relationship was observed between matrix resilience ($M_R$) and firmness ($M_F$) while an inverse association existed with the energy of matrix distortion ($C_D$). In other words, an increase in resilience generated an increase in matrix firmness and a decrease in the energy of matrix distortion. Furthermore, formulations (Formulations 1, 2, 4, 7, 12, 13) containing higher levels of the matrix stiffeners (polyvinyl alcohol; PVA, magnesium stearate; MS and ethylcellulose; ETH) had elevated $M_R$ and $M_R$ and reduced $\epsilon_D$ values while the converse was observed for formulation with low levels of the matrix stiffeners (Formulations 3, 5, 11, 12, 14, 15). The numerical values of physicomechanical parameters also show that the matrices have low elasticity or recovery (from external stress) tendencies and resistance to deformation (Table 8) which may be due to their porous structure characterized by the presence of void spaces within the matrix.

TABLE 8

Matrix resilience, distortion and firmness numerical values for the P-ECMs

| Formulation | $^a$M$_R$ (%) | $^b\epsilon_D$ (J) | $^c$M$_F$ (N/mm) |
|---|---|---|---|
| 1 | 2.975 | 0.052 | 4.430 |
| 2 | 2.230 | 0.033 | 5.214 |
| 3 | 2.080 | 0.014 | 5.449 |
| 4 | 2.221 | 0.049 | 5.168 |
| 5 | 2.065 | 0.018 | 5.518 |
| 6 | 2.195 | 0.053 | 4.991 |
| 7 | 2.288 | 0.058 | 4.904 |
| 8 | 2.101 | 0.034 | 4.671 |
| 9 | 1.590 | 0.052 | 3.404 |
| 10 | 2.067 | 0.034 | 4.889 |
| 11 | 2.069 | 0.015 | 5.550 |
| 12 | 2.142 | 0.042 | 5.006 |
| 13 | 2.253 | 0.035 | 4.824 |
| 14 | 1.024 | 0.046 | 4.082 |
| 15 | 1.922 | 0.023 | 4.998 |

$^a$Matrix resilience,
$^b$energy of matrix distortion,
$^c$matrix firmness

DEE for the dosage form ranged from 55-86% with an average of 72% (FIG. 18).
Drug loading capacity of the formulations Effective drug loading was achieved with values ranging from 53.14±2.19% to 99.02±0.74% (Table 9).

TABLE 9

Drug loading capacity of the 15 formulations

| Formulation No. | | Drug Loading Capacity (%) |
|---|---|---|
| 1 | Formulation Number | 58.599 |
| 2 | | 80.535 |
| 3 | | 95.1404 |
| 4 | | 99.095 |
| 5 | | 94.637 |
| 6 | | 99.019 |
| 7 | | 97.536 |
| 8 | | 66.833 |
| 9 | | 83.271 |
| 10 | | 79.284 |
| 11 | | 94.848 |
| 12 | | 98.637 |
| 13 | | 53.137 |
| 14 | | 81.378 |
| 15 | | 79.179 |

Ex Vivo Bioadhesion Testing

The capability of the formulations to adhere to a model biological tissue (porcine buccal mucosa) was made evident by the values obtained for the peak force of detachment ($F_{det}$) (0.9636±0.015N to 1.042±0.025N) and work or energy of adhesion ($w_{adh}$) (0.0014±0.00005 J to 0.0028±0.00008 J) (FIG. 19). No specific trend was observed with the differences in the quantities of the bioadhesive compounds (gelatin and carbopol) included during the preparation of the formulations. It can be proposed that gelatin and carbopol complemented each other in influencing the overall adhesion characteristics of the matrices. This explains why all the formulations showed a level bioadhesive competence. Also, particular patterns directly or inversely relating $F_{det}$ to $w_{adh}$ were absent. This implies that the $F_{det}$ did not specifically influence the values of $w_{adh}$. This may be attributable to the fact that the energy expended during bioadhesion or the force of detachment are extensively influenced by the inter-surface electrostatic interactions between the matrices, tissue and simulated saliva that may be dependent on the proportions of the bioadhesive as well as other co-particles present within each matrix.

Matrix Surface Morphology

Scanning electron microscopy showed the varieties of pore structures, distributions and interconnections displayed by the matrices with some that were relatively alike as well. Their surface porous configuration was rather complex, irregular and extensive (FIG. 20). Generally, the kinds of pore structures observed ranged from circular (FIGS. 20 (b, c, e, h, k, m and o) to those with asymmetrical geometries or shapes (FIGS. 20 a, d, f, g, l, j and n). The pores were comparatively widespread through the surface of the matrices. The interconnections which can be described as barriers or partitions that demarcate the pores were rather uneven and exhibited rigid (FIGS. 20 f, g, j and n), web-like/thread-like (FIGS. 20 b, c, e, h, k, m and o) and spongy (FIGS. 20 a, d and i) structures.

Furthermore, a relationship between the surface morphology and the drug release characteristics of the matrices was observed. It was observed that the pore interconnections played a noticeable role in their drug release performances. Matrices with web-like, thread-like and spongy interconnections (FIGS. 20 a, b, c, d, e, h, i, k, m, and o representing Formulations 1, 2, 3, 4, 5, 8, 9, 11, 13 and 15) demonstrated quicker but controlled release rates with over 65% drug released over 8 hours (FIG. 4). The converse was observed with formulation that exhibited rigid interconnections such as FIGS. 20 f, g, j and n representing Formulations 6, 7, 10 and 14 respectively in which case drug release was slower with less than 65% liberated over 8 hours. Consequently, a hypothesis that the interconnections function as barriers within porous matrices and play the role of regulating matrix hydration, disentanglement, diffusion of drug and erosion can be made.

The quantity of pore-forming agent added when preparing the matrices has been noted to have a major influence on the porosity characteristics of the matrices. In addition, ethanol presents to be a more potent pore forming agent than water with respect to this study as slight increment in the volume of ethanol resulted in visible changes in pore structure (i.e. enhanced porosity). For instance, Formulations 2, 3, 5, and 11 containing highest levels of ethanol (13 mL and 15 mL) displayed larger and higher volume of pores (FIGS. 6 a, b, c, e and f respectively) when compared with formulations 1, 4 and 15 (FIGS. 6 a, d and o) with highest volume of water (30 mL) giving rise to lower volumes of pores. With Formulations 7, 12 and 14 composed of low levels of ethanol (10 mL), pore distribution is lower signified with the presence of more rigid interconnections (FIGS. 6 a, g, l and n). In addition, Formulations 6, 8, 9, 10 and 13 (FIGS. 6 f, h, l, j and m) are exceptions to this trend and this may be due to influence of the co-particulate components on the sublimation of the pore-forming agents from the matrices during the process of lyophilization.

Permeation of Drug Through the Porcine Buccal Mucosa

The permeation enhancing capability of the formulations was investigated and results presented in FIGS. 21 and 22 as cumulative drug penetration (%) and drug flux (mg cm$^{-2}$ min$^{-1}$) respectively over 8 hours for the 15 formulations. The drug flux values were calculated using Equation 2. Overall, the formulations showed diverse permeation enhancing capabilities as different amounts (percentage) of drug molecules passed through the tissue within the set experimentation time (FIG. 21).

Different levels of each permeation enhancer (sorbitan ester 80, chitosan and menthol) had complex co-interactive, combined influences on the other but a relatively coherent general pattern of impact on permeation enhancement was noticed. In summary, the permeation enhancers were observed to be most efficient at mid to low levels (Formulations 1, 2, 3, 5, 8, 9, 11, 13, 14 and 15) while the converse is applicable to highest level of the enhancers (Formulations 4, 7 and 12). Some exceptions to the stated trend included Formulations 6 and 10.

Flux could be described as the rate of drug permeation per unit surface area. The formulations demonstrated differences in their in their flux which may be due to complex interaction between the permeation enhancers as well as other components within each matrix. With respect to this study, an independent, non-linear relationship existed between the quantity of drug that permeated through the tissue into the recipient compartment and the drug flux (FIG. 22). In other words, the rate at which the drug molecules permeate through the tissue (flux) was not a determining factor for the amount of drug that will eventually be detected in the recipient compartment.

Measurement of Matrix Porosity Qualitatively

The outcome of this study showed that all the formulations are porous with values ranging from 74.93% to 86.12% (FIG. 23). With pores being the void spaces within the matrix, porosity in this case measures the influx of water molecules into the matrix to fill the empty spaces or pores. Consequently, an increase in the numerical value of qualitative porosity should be indicative of a more porous matrix and vice versa (FIG. 23). To further evaluate the impact of the varying porosity values obtained for the formulations, a comparison was made with their drug release characteristics and surface morphology. Generally, formulations with lower porosity values 579.90% (Formulations 1, 6, 7, 12 and 14) displayed slower release rates when compared with those with higher porosity values >80.49% (Formulations 2, 8, 9 and 10) showed faster rates of drug release (FIG. 23).

Some exclusion to this outcome included Formulations 3, 11, 13 and 15 with lower and Formulation 4 with higher porosity values but demonstrated faster and slower release rates respectively. This reverse in behavior could be as a result of the influence of the pore interconnections of each matrix. Therefore, a hypothesis stating that the in addition to the pore structures, the nature of the pore interconnections can also influence influx of water, hydration and disentanglement of these matrices which subsequently affect qualitative matrix porosity and drug release in diverse ways can be put forward.

Structural Transformations during Preparation FTIR studies were done to detect the possible interactions between the compounds and drug in the preparation of the matrices. The FTIR spectra of each formulation showed a similar pattern to the other (FIG. 24) with slight variations in their peaks which an indication of differences in transmittance values attributable to the variations in the concentration of each component included for the preparation of the matrices. Consequently, it can be proposed that no transforming irreversible, chemical interaction took place among the components during the preparation of the formulations. In other words, the co-particulate blend seemed to be only a summation of drug and other compounds and that each component maintained its physicochemical characteristics during the process of preparation.

Conclusions

The multi-configured pharmaceutical dosage form produced may be suitable for transmucosal drug delivery based on its flexibility to achieve rapid and/or prolonged drug release and relatively complete disintegration, implying rapid liberation of drug for systemic absorption. In addition to this, the novelty of the system's layering effect renders it potentially useful for the delivery of more than one drug in a single dosage form. Rapid drug delivery employing porous matrices is an advancing field. In addition to being relatively cost-effective and simple to manufacture, they are also a highly efficient, versatile, and effective means of drug delivery. This is largely due to being able to use the dosage form via the transmucosal route to provide patients with rapid or prolonged, easy, and non-invasive drug therapy. Demand by the pharmaceutical industry for researching novel methods of enhancing drug delivery via porous matrix technology is enormous. This may provide an advantageous position in the market, especially with regard to the reformulation of currently used antiretrovirals, analgesics, antihistamines, anti-emetics, anti-inflammatories, anti-diarrheals, multivitamins, minerals, trace elements, phytonutrients and sedatives that require rapid or prolonged onset of action. Drugs incorporated into the multi-configured dosage form produced would also be beneficial for individuals who find swallowing tablets and/or receiving injections problematic, such as paediatric patients requiring anti-retrovirals or colic medication, geriatrics, unconscious patients and patients confined to intensive care units.

This work provides valuable information that can be employed in developing such novel porous-enabled composite multi-layered and/or monolithic matrices for application in transmucosal drug delivery employing the buccal mucosa as a model. The impact of porosity (pore structure, interconnections, pore width and pore volume of distribution) and overall preparation technique on the physicochemical strength, drug loading capacity and release, permeation enhancement, surface configuration, rheology and bioadhesive capacity was established. Interphase, co-particulate, co-solvent, homogenization and lyophilization, the methods employed for the construction of the pore-regulated matrices had no irreversible distorting influence on the stability, flexibility and viscoelasticity of the blend which indicates the efficiency of these methods as carriers retained the contributive effects of individual chemical compound make-up of the formulations. Furthermore, the resultant crosslinked lyophilized systems could allow for controlled delivery of the incorporated drug for gradual transmucosal drug delivery. The multi-configured pharmaceutical dosage form was successfully designed. The investigated physicochemical and physicomechanical properties revealed the potential of this matrix to be applied for prolonged, transmucosal drug delivery. The distinct flexible characteristics observed with the formulations imply that porosity-enabled matrix can be versatile which makes it attractive for adapted invention and construction of drug delivery systems.

REFERENCES

1. Sastry S V, Nyashadham J R, Fix J A. Recent technological advances in oral drug delivery—a review. Pharmaceutical Science and Technology Today. 2000; 3(4): 138-145.
2. Virley P and Yarwood R. Zydis—a novel, fast-dissolving dosage form. Journal of Manufacturing Chemistry. 1990; 61: 36-37.
3. Dobetti L. Fast-melting tablets: developments and technologies. Pharmaceutical Technology Europe. 2000; 12(9): 32-42.

4. Lindgren S, Janzon L. Dysphagia: prevalence of swallowing complaints and clinical findings. Journal of Medicinal Clinics of North America. 1993; 77: 3-5.
5. Habib W, Khankari R, Hontz J. Fast-dissolving drug delivery systems, clinical review in therapeutics. Journal of Drug Carrier Systems. 2000; 17(1): 61-72.
6. Fox D A. Rapid-dissolving dosage forms: an expanding therapeutic approach. Paper presented at the 1996 Drug Delivery Systems Workshop at the Institute of International Research.
7. Chang R, Guo X, Burnside B A, et al. Fast-dissolving tablets. Journal of Pharmaceutical Technology. 2000; 24(6): 52-58.
8. Thummel K E, Kunze K L, Shen D D. Enzyme-catalyzed processes at first-pass hepatic and intestinal drug extraction. Journal of Advanced Drug Delivery. 1997; 27: 99-127.
9. Artusi M, Santi P, Colombo P, at al. Buccal delivery of thiocolchicoside: in vitro and in vivo permeation studies. International Journal of Pharmaceutics. 2003; 250(1): 203-213.
10. Sudhakar Y, Kuotsu K, Bandyopadhyay A K. Buccal bioadhesive drug delivery—a promising option for orally less efficient drugs. Journal of Controlled Release. 2006; 114(1): 15-40.
11. Morishita M, Peppas N A. Is the oral route possible for peptide and protein delivery? Drug Discovery Today. 2006; 11(19-20): 905-910.
12. Harris D, Robinson J R. Drug delivery via the mucous membranes of the oral cavity. Journal of Pharmaceutical Science. 1992; 81: 1-10.
13. Rathbone M J, Drummond B K, Tucker I G. The oral cavity as a site for systemic drug delivery. Advanced Drug Delivery Reviews. 1994; 13(1-2): 1-22.
14. Bredenberg S, Duberg M, Lennernas B, et al. In vitro and in vivo evaluation of a new sublingual tablet system for rapid oramucosal absorption using fentanyl citrate as the active substance. European Journal of Pharmacy and Biopharmaceutics. 2003; 20: 327-334.
15. Harris D, Robinson J R. Drug delivery via the mucous membranes of the oral cavity. Journal of Pharmaceutical Science. 1992; 81: 1-10.
16. Nicolazzo J A, Reed B L, Finnin B C. Buccal penetration enhancers—how do they really work? Journal of Controlled Release. 2005; 105(1-2): 1-15.
17. Senel S and Huncal A A. Drug permeation enhancement via buccal route: possibilities and limitations. Journal of Controlled Release. 2001; 72(1-3): 133-144.
18. Bogner R H and Wilkosz M F. Fast-dissolving tablets. http://www.uspharmacist.com/oldformat.asp?url=newlook/files/feat/fastdissolving.htm Accessed on 17 Aug. 2007.
19. Brown D. Orally disintegrating tablets: taste over speed. Drug Delivery Technology. 2001; 3(6): 58-61.
20. Aurora J and Pathak V. Oral disintegrating technologies: oral disintegrating dosage forms: an overview. Drug Delivery Technology. 2005; 5(3): 50-54.
21. Needleman I. G, Smales F. C. In vitro assessment of bioadhesion for periodontal and buccal drug delivery. Biomaterials. 1995; 16: 617-624.
22. Pontero A, Teijeiro-Osorio D, Alonso M J, Reuman L. Development of chitosan sponges for buccal administration of insulin. 2006, Department of Pharmacy, Spain.
23. Luo K, Yin J. Mucoadhesive and elastic films based on blends of chitosan and H EC. Macromolecular Bioscience. 2008; 8: 184-192.
24. Ahmed, A., Bonner, C. and Dessai, C. (2002). Bioadhesive microdevices with multiple reservoirs: a new platform for oral drug delivery. *J. Control. Release.;* 81: 291-306.
25. Akkar, A. and Müller, R. H. (2003). Formulation of intravenous Carbamazepine emulsions by SolEmuls® technology. *Eur. J. Pharm. Biopharm.;* 55: 305-312.
26. Alur, H. H., Johnston, T. P. and Mitra, A. K. (2001). In "Encyclopedia of Pharmaceutical Technology", ed. Superbrick, J., Boylan, J. C. in *Peptides and proteins: Buccal absorption,* 20(3): 193-218.
27. Alvarez-Núñez, F. A. and Yalkowsky, S. H. (1999). Buffer capacity and precipitation control of pH solubilzed phenytoin formulations. *Int. J. Pharm.;* 195: 45-49.
28. Attia, M. A., E I-Gibaly, I., Shaltout, S. E. and Fetih, G. N. (2004). Transbuccal permeation, anti-inflammatory activity and clinical efficacy of piroxicam formulated in different gels. *International Journal of Pharmaceutics.;* 276: 11-28.
29. Berger, J., Reist, M., Mayer, J. M., Felt, O. and Gurny, R. (2004). Structure and interactions in chitosan hydrogels formed by complexation or aggregation for biomedical applications. *Eur. J. Pharm. Biopharm.;* 57: 35-52.
30. Berressem, P. (1999). Controlled release of oral dosage forms. *Pharm. Tech.;* 6: 10-16.
31. Brannon-Peppas, L. (1997). Polymers in controlled drug delivery. *Medical Plastics and Biomaterials Magazine.* M PB Article Index, pgs 1-15.
32. Chien, Y. W. (2006). In "Novel drug delivery systems", in *Drugs and the Pharmaceutical Sciences.* 50: 197-200.
33. Colombo, P., Bettini, R., Santi, P. and Peppas, N. A. (2000). Swellable matrices for controlled drug delivery: gel-layer behaviour, mechanisms and optimal performance. *P SST.;* 3: 198-204.
34. Das, N. G. and Das, S. K. (2003). Controlled release of oral dosage forms. *Pharm. Tech.;* 6: 10-16.
35. Hoa, M. L. K., Lu, M. and Zhang, Y. (2006). Preparations of porous materials with ordered hole structure. *Advan. Coll. Interf. Sci;* 121: 9-23.
36. Jamzad, S., Tutunji, L. and Fassihi, R. (2005). Analysis of macromolecular changes and drug release from hydrophilic matrix systems. *Int. J. Pharm.;* 292: 75-85.
37. Lee, V. H. L. (1988). Enzymatic barriers to peptide and protein absorption. *Crit. Rev. Ther. Drug Carrier Syst.,* 5: 69-97.
38. Liu, L., Fishman, M. L., Kost, J. and Hicks, K. B. (2003). Pectin-based systems for colon specific drug delivery via oral route. *Biomaterials.;* 24: 3333-3343.
39. Lu, Y., and Chen, S. C. (2004). Micro and nano-fabrication of biodegradable polymers for drug delivery. *Adv. Drug. Del. Rev.;* 56: 1621-1633.
40. Moon Suk K., Kwang Su S., Hoon H., Sun Kyung K., Gilson K. and Hai Bang L. (2005). Sustained release of bovine serum albumin using implantable wafers prepared by M PEG-PLGA diblock copolymers. *International Journal of Pharmaceutics.;* 304:165-177.
41. Müler, R. H., Mader, K. and Gohla, S. (2000). Solid lipid nanoparticles (SLN) for controlled drug delivery—a review of the state of the art. *Eur. J. Pharm. Biopharm.;* 50: 161-177.
42. Orive, G., Hernandez, R. M., Gascon, A. R., DominguezGily, A. and Pedraz, J. L. (2003). Drug delivery in biotechnology: present and future. *Current Opinion Biotech.;* 14: 659-664.
43. Pellock, J. M., Smith, M. C., Cloyd, J. C., Uthman, B, and Wilder, B. J. (2004). Extended-release formulations: simplifying strategies in the management of antiepileptic drug therapy. *Epilepsy Behav.;* 5: 301-307.

44. Ponchel, G., Montisci, M., Dembri, A., Durrer, C. and Duchêne, D. (1997). Mucoadhesion of colloidal particulate systems in the gastro-intestinal tract. *Eur. J. Pharm. Biopharm.;* 44: 25-31.

45. Rodríguez-Lorenzo L. M. and Ferreira J. M. F. (2004). Development of porous ceramic bodies for applications in tissue engineering and drug delivery systems. *Materials Research Bulletin;* 39: 83-91.

46. Sher, P., Ingavle, G. Ponrathnam, S. and Pawar, A. P. (2007). Low density porous carrier drug absorption and release study by response surface methodology using different solvents. *Int. J. Pharm.;* 331: 72-83.

47. Sinha, V. R. and Khosla, L. (1998). Bioabsorbable polymers for implantable therapeutic systems. *Drug Dev. Ind. Pharm.;* 24: 38.

48. Smart, J. D. (2005). The basics and underlying mechanisms of mucoadhesion. *Adv. Drug. Del. Rev.;* 57: 1556-1568.

49. Steward, P. A. (1995). A literature review of pharmaceutical controlled release methods and devices, <http://www.initium.demon.co.uk/rel_nf.htm>. [Accessed: 01.04.2007].

50. Sudhakar, Y., Kuotsu, K. and Bandyopadhyay, A. K. (2006). Buccal bioadhesive drug delivery-a promising option for orally less efficient drugs. *J. Control. Release.;* 114: 15-40.

51. Tang C., Yin C., Pei, Y., Zhang M., Wu, L. (2005) New superporous hydrogels composites based on aqueous Carbopol® solution (SPHCcs): synthesis, characterization and in vitro bioadhesive force studies. *European Polymer Journal.;* 41:557-562.

52. Tao, S. L. and Desai, T. A. (2003). Microfabricated drug delivery systems: from particles to pores. *Adv. Drug. Del. Rev.;* 55: 315-328.

53. Wang, X. and Patsalos, P. N. (2003). A comparison of central brain (cerebrospinal and extracellular fluids) and peripheral blood kinetics of phenytoin after intravenous phenytoin and fosphenytoin. *Seizure.;* 12: 330-306.

54. Zhang, J., Niu, S., Ebert, C. and Stanley, T. H. (1994). An in vivo model for studying recovery kinetics of the buccal mucosa permeation barrier after exposure to permeation enhancers: apparent evidence of effective enhancement without tissue damage. *International Journal of Pharmaceutics.;* 101: 15-22.

55. Sohier, J., Vlugt, T. J. H, Cabrol, N, Van Blitterswijk, C., de Groot, K. and Bezemer, J. M. (2006). Dual release of proteins from porous polymeric scaffolds. *J. Control Release.;* 111: 95-106.

56. Sher, P., Ingavle, G. Ponrathnam, S. and Pawar, A. P. (2007). Low density porous carrier drug absorption and release study by response surface methodology using different solvents. *Int. J. Pharm.;* 331: 72-83.

57. Wang, Y., Chang, H., Wertheim, D. F., Jones, A. S., Jackson, C. and Coombes, A. G. A. (2007). Characterisation of the macroporosity of polycaprolactone-based biocomposited and release kinetics for drug delivery. *Biomaterials;* 28: 4619-4627.

58. Portero, A., Teijeiro-Osorio, D., Alonso, M. J., Remunan-Lopez. (2007). Development of chitosan sponges for buccal administration of insulin. *Carbohydrate Polymers;* 68: 617-625.

59. Chu, L., Liang, Y., Chen, W, Ju, X. and Wang, H. (2004). Preparation of glucose-sensitive microcapsules with porous membrane and functional gates. *Colloids and Surfaces B: Biointerfaces;* 37: 9-14.

60. Matthews, K. H., Stevens, H. N. E., Auffret, A. D., Humphrey, M. J. and Eccleston, G. M. (2006). Gamma-irradiation of lyophilized wound healing wafers. *International Journal of Pharmaceutics;* 313:78-86.

61. Miao, X., Hu, Y., Liu, J. and Wong, A. P. (2004). Porous calcium phosphate ceramics prepared by coating polyurethane foams with calcium phosphate cements. *Materials Letters;* 58:397-402.

62. Park, Y. J., Nam, K. H, Ha, S. J., Pai, C. M., Chung, C. P. and Lee, S. J. (1997). Porous poly(L-lactide) membranes for guided tissue regeneration and controlled drug delivery: membrane fabrication and characterization. *Journal of Controlled Release;* 43: 151-160.

63. Åkerman, S., Viinikk, P. Svarfvar, B. Jarvinen, K., Kontturi, K and Nasman, J. (1998). Transport of drugs across porous ion exchange membranes. *Journal of Controlled Release;* 50: 153-166.

64. Netz, D. J. A., Sepulveda, P., Pandolfelli, V. C. and Spadaro, A. C. C., Alencastre, J. B., Bentley, M. V. L. B., Marchetti, J. M. (2001). Potential use of gelcasting hydroxyapatite porous ceramic as an implantable drug delivery system. *International Journal of Pharmaceutics;* 213: 117-125.

65. Li, Z., Wen, L., Shao, L. and Chen, J. (2004). Fabrication of porous hollow silica nanoparticles and their applications in drug release control. *Journal of Controlled Release;* 98: 245-254.

66. Kim, H., Knowles, J. C. and Kim, H. (2004). Hydroxyapatite/poly(e-caprolactone) composite coatings on hydroxyapatite porous bone scaffold for drug delivery. *Biomaterials;* 25: 1279-1287.

67. Bromberg, L. E., Buxton, D. K. and Friden, P. M. (2001). Novel periodontal drug delivery system for the treatment of periodontitis. *Journal of Controlled Release;* 71: 251-259.

68. Patel, R., Pillay, V., Choonara, Y. E. and Govendar, Thirunula. (2007). A Novel Cellulose-Based Hydrophilic Wafer Matrix for Rapid Bioactive Delivery. *Journal of Bioactive and Compatible Polymers;* 22:119-142.

69. Peh, K. K. and Wong, C. F. (1999). Polymeric films as vehicle for buccal delivery: swelling, mechanical and bioadhesive properties. *Journal of Pharm and Pharmaceut. Sci.;* 2: 53-61.

70. Giannola L. I., De Caro V., Giandalia, G., Siragusa, M. G., Tripodo, C. Florena, A. M. and Campisi, G. (2007). Release of naltrexone on buccal mucosa: Permeation studies, histological aspects and matrix system design. *European Journal of Pharmaceutics and Biopharmaceutics;* 67: 425-433.

71. Van Eyk, A. D. and Thompson I. O. C. (1998). Effects of freezing on the permeability of human buccal and vaginal mucosa. *S. Afr. J. Sci.;* 94:499-502.

72. Van der Bijl, P., Van Eyk, A. D., Thompson, I. O. C. and Stander, L A. (1998). Diffusion rates of vasopressin through human vaginal and buccal mucosa. *Eur. J. Oral Sci.,* 106: 958-962.

73. Van Eyk, A. D. and Van der Bijl. (2004). Comparative permeability of various chemical markers through human vaginal and buccal mucosa as well as porcine buccal and mouth floor mucosa. *Archives of Oral Biology;* 49:387-392.

74. Consuelo, D. D., Pizzolato, G. P., Falson, F., Guy, R. H. and Jacques, Y. (2005). Evaluation of pig esophageal mucosa as a permeability barrier model for buccal tissue. *J. Pharm. Sci.;* 94: 2777-2788.

75. Mehta, K. A., Kislalioglu, M. S., Phuapradit, W., Malick, A. W., Shah, N. H. (2000). Effects of formulation and process variables on porosity parameters and release rates from a multi unit erosion matrix of a poorly soluble drug. *Journal of Controlled Release.;* 63: 201-211.
76. Dourdain, S., Mehdi, A., Bardeau, J. F. and Gibaud, A. (2006). Determination of porosity of mesoporous silica thin films by quantitative x-ray reflectivity analysis and GISAXS. *Thin Solid Films;* 495: 205-209.
77. Pillay, V. and Fassihi, R. (1998). Evaluation and comparison of dissolution data derived from different modified release dosage forms: an alternative method. *J. Control Release.;* 55: 45-55.
78. Rinaki, E., Dokoumetzidis, A., and Macheras, P. (2003). The mean dissolution time depends on the dose/solubility ratio. *Pharmaceutical Research;* 20:406-408.
79. Ansari, M., Kazemipour M. and Talebria, J. (2004). The development and validation of a dissolution method for clomipramine solid dosage forms. *Dissolution Technologies*, August edition, pages 17; 20-24.
80. Repka, M. A., Gutta, K., Prodduturi, S., Munjal, M. and Stodghill, S. P. (2005). Characterization of cellulosic hot-melt extruded films containing lidocaine. *European Journal of Pharmaceutics and Biopharmaceutics;* 59:189-196.
81. Kumar, T. M., Paul, W., Sharma, C. P. and Kuriachan, M. A. (2005). Bioadhesive, pH responsive micro-matrix for oral delivery of insulin. *Trends in Biomaterials and Artificial Organs;* 18:198-202.
82. Martin, L., Wilson, C. G., Koosha, F. and Uchegbu, I. F. (2005). Sustained buccal delivery of the hydrophobic drug, denbufylline using physically cross-linked palmitoyl glycol chitosan hydrogels. *European Journal of Pharmaceutics and Biopharmaceutics;* 55: 35-45.
83. Kim, T. H., Ahn, J. S., Choi, H. K., Choi, Y. J. and Cho, .C. S. (2007). A novel mucoadhesive polymer film composed of carbopol, poloxamer and hydroxypropoylmethylcellulose. *Archives of Pharmacal Research;* 30: 381-386.
84. Zhang, Y., Wang, Y., Shi, B. and Cheng, X. (2007). A platelet-derived growth factor releasing chitosan/coral composite scaffold for periodontal tissue engineering. *Biomaterials;* 28:1515-1522.
85. Shojael, A. H., Chang, R. K., Guo, X., Burnside, B. A. and Couch, R. A. (2001). Systemic drug delivery via the buccal mucosal route. *Pharmaceutical Technology;* 70-81. <www.pharmaportal.com>, [Accessed on the 14 Apr. 2007]

The invention claimed is:

1. A bilayered transmucosal buccal pharmaceutical dosage form, wherein the dosage form consists of:
a porous cellulosic layer that forms a gel upon contact with a bodily fluid, the gel forming a diffusive barrier; and
a granular layer of chitosan that disintegrates more rapidly than the cellulosic layer upon contact with the bodily fluid; and
a pharmaceutically active compound, wherein the pharmaceutical dosage form delivers the pharmaceutically active compound to a buccal mucosal surface,
wherein the cellulosic layer and the granular layer are crosslinked with a crosslinking agent selected from a metal salt or a salt of the Hofmeister series of salts.

2. The dosage form of claim 1, wherein the cellulosic layer is hydroxypropyl cellulose (HPC).

3. The dosage form of claim 2, wherein the dosage form is obtained by freezing a suspension in which chitosan and HPC solutions having equal concentrations of chitosan and HPC, respectively, are combined in a 2:1 ratio.

* * * * *